United States Patent
Petrukhin et al.

(10) Patent No.: US 7,179,620 B2
(45) Date of Patent: Feb. 20, 2007

(54) GENE RESPONSIBLE FOR STARGARDT-LIKE DOMINANT MACULAR DYSTROPHY

(75) Inventors: Konstantin Petrukhin, Collegeville, PA (US); Wen Li, San Diego, CA (US); Kang Zhang, Salt Lake City, UT (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/477,042

(22) Filed: Jun. 28, 2006

(65) Prior Publication Data

US 2006/0246048 A1    Nov. 2, 2006

Related U.S. Application Data

(62) Division of application No. 10/276,732, filed on Oct. 3, 2003, now Pat. No. 7,091,005.

(60) Provisional application No. 60/204,990, filed on May 16, 2000.

(51) Int. Cl.
C07H 21/04    (2006.01)
C12N 1/20    (2006.01)
C12N 15/00    (2006.01)

(52) U.S. Cl. ............... 435/69.1; 435/252.3; 435/320.1; 536/23.1

(58) Field of Classification Search ............... 435/69.1, 435/252.3, 320.2; 536/23.1
See application file for complete search history.

(56) References Cited

U.S. PATENT DOCUMENTS 7,091,005 B2 *    8/2006    Petrukhin et al. .......... 435/69.1

\* cited by examiner

*Primary Examiner*—Tekchand Saidha
(74) *Attorney, Agent, or Firm*—Joan E. Switzer; Joanne M. Giesser

(57) ABSTRACT

The gene responsible for Stargardt-like macular dystrophy has been identified, along with its normal allelic form. The mutant gene encodes a mutant protein containing a frameshift mutation, resulting in abnormal fatty acid synthesis and transport in the retina. Also disclosed are assays for Stargardt-like macular dystrophy and therapies.

8 Claims, 17 Drawing Sheets

SEQ.ID.NO.1

| | |
|---|---|
| 1-40 | MGLLDSEPGSVLNVVSTALNDTVEFYRWTWSIADKRVENW |
| 41-80 | PLMQSPWPTLSISTLYLLFVWLGPKWMKDREPFQMRLVLI |
| 81-120 | IYNFGMVLLNLFIFRELFMGSYNAGYSYICQSVDYSNNVH |
| 121-160 | EVRIAAALWWYFVSKGVEYLDTVFFILRKKNNQVSFLHVY |
| 161-200 | HHCTMFTLWWIGIKWVAGGQAFFGAQLNSFIHVIMYSYYG |
| 201-240 | LTAFGPWIQKYLWWKRYLTMLQLIQFHVTIGHTALSLYTD |
| 241-280 | CPFPKWMHWALIAYAISFIFLFL*NFYI*RTYKEPKKPKAGK |
| 281-315 | *TAMNGISANGVSKSEKQLMIENGKKQKNGKAKGD* |

FIG.1

Mutant human ELF protein
(SEQ.ID.NO. 2)

| | |
|---|---|
| 1-40 | MGLLDSEPGSVLNVVSTALNDTVEFYRWTWSIADKRVENW |
| 41-80 | PLMQSPWPTLSISTLYLLFVWLGPKWMKDREPFQMRLVLI |
| 81-120 | IYNFGMVLLNLFIFRELFMGSYNAGYSYICQSVDYSNNVH |
| 121-160 | EVRIAAALWWYFVSKGVEYLDTVFFILRKKNNQVSFLHVY |
| 161-200 | HHCTMFTLWWIGIKWVAGGQAFFGAQLNSFIHVIMYSYYG |
| 201-240 | LTAFGPWIQKYLWWKRYLTMLQLIQFHVTIGHTALSLYTD |
| 241-272 | CPFPKWMHWALIAYAISFIFL*FLLHSDIQRA* |

FIG.2

Human *ELF* cDNA (SEQ.ID.NO. 3) and
Amino acid (SEQ.ID.NO. 1)

```
  1  CGCCGCGATGGGGCTCCTGGACTCGGAGCCGGGTAGTGTCCTAAACGTAGTGTCCACGGC   60
  1          M  G  L  L  D  S  E  P  G  S  V  L  N  V  V  S  T  A    18

61  ACTCAACGACACGGTAGAGTTCTACCGCTGGACCTGGTCCATCGCAGATAAGCGTGTGGA  120
 19   L  N  D  T  V  E  F  Y  R  W  T  W  S  I  A  D  K  R  V  E    38

121  AAATTGGCCTCTGATGCAGTCTCCTTGGCCTACACTAAGTATAAGCACTCTTTATCTCCT  180
 39   N  W  P  L  M  Q  S  P  W  P  T  L  S  I  S  T  L  Y  L  L    58

181  GTTTGTGTGGCTGGGTCCAAAATGGATGAAGGACCGAGAACCTTTTCAGATGCGTCTAGT  240
 59   F  V  W  L  G  P  K  W  M  K  D  R  E  P  F  Q  M  R  L  V    78

241  GCTCATTATCTATAATTTTGGGATGGTTTTGCTTAACCTCTTTATCTTCAGAGAGTTATT  300
 79   L  I  I  Y  N  F  G  M  V  L  L  N  L  F  I  F  R  E  L  F    98

301  CATGGGATCATATAATGCGGGATATAGCTATATTTGCCAGAGTGTGGATTATTCTAATAA  360
 99   M  G  S  Y  N  A  G  Y  S  Y  I  C  Q  S  V  D  Y  S  N  N   118

361  TGTTCATGAAGTCAGGATAGCTGCTGCTCTGTGGTGGTACTTTGTATCTAAAGGAGTTGA  420
119   V  H  E  V  R  I  A  A  A  L  W  W  Y  F  V  S  K  G  V  E   138

421  GTATTTGGACACAGTGTTTTTTATTCTGAGAAAGAAAAACAACCAAGTTTCTTTCCTTCA  480
139   Y  L  D  T  V  F  F  I  L  R  K  K  N  N  Q  V  S  F  L  H   158

481  TGTGTATCATCACTGTACGATGTTTACCTTGTGGTGGATTGGAATTAAGTGGGTTGCAGG  540
159   V  Y  H  H  C  T  M  F  T  L  W  W  I  G  I  K  W  V  A  G   178

541  AGGACAAGCATTTTTTGGAGCCCAGTTGAATTCCTTTATCCATGTGATTATGTACTCATA  600
179   G  Q  A  F  F  G  A  Q  L  N  S  F  I  H  V  I  M  Y  S  Y   198

601  CTATGGGTTAACTGCATTTGGCCCATGGATTCAGAAATATCTTTGGTGGAAACGATACCT  660
199   Y  G  L  T  A  F  G  P  W  I  Q  K  Y  L  W  W  K  R  Y  L   218

661  GACTATGTTGCAACTGATTCAATTCCATGTGACCATTGGGCACACGGCACTGTCTCTTTA  720
219   T  M  L  Q  L  I  Q  F  H  V  T  I  G  H  T  A  L  S  L  Y   238

721  CACTGACTGCCCCTTCCCCAAATGGATGCACTGGGCTCTAATTGCCTATGCAATCAGCTT  780
239   T  D  C  P  F  P  K  W  M  H  W  A  L  I  A  Y  A  I  S  F   258

781  CATATTTCTCTTTCTTAACTTCTACATTCGGACATACAAAGAGCCTAAGAAACCAAAAGC  840
259   I  F  L  F  L  N  F  Y  I  R  T  Y  K  E  P  K  K  P  K  A   278

841  TGGAAAAACAGCCATGAATGGTATTTCAGCAAATGGTGTGAGCAAATCAGAAAAACAACT  900
279   G  K  T  A  M  N  G  I  S  A  N  G  V  S  K  S  E  K  Q  L   298

901  CATGATAGAAAATGGAAAAAAGCAGAAAAATGGAAAAGCAAAAGGAGATTAAATTGAACT  960
299   M  I  E  N  G  K  K  Q  K  N  G  K  A  K  G  D  *           315

961  GGGCCTTAACTG  972
```

FIG.3

Human *ELF* cDNA, mutant (SEQ.ID.NO. 4) and
Amino acids (SEQ.ID.NO. 2)

```
  1  CGCCGCGATGGGGCTCCTGGACTCGGAGCCGGGTAGTGTCCTAAACGTAGTGTCCACGGC   60
  1          M  G  L  L  D  S  E  P  G  S  V  L  N  V  V  S  T  A    18

61  ACTCAACGACACGGTAGAGTTCTACCGCTGGACCTGGTCCATCGCAGATAAGCGTGTGGA  120
 19     L  N  D  T  V  E  F  Y  R  W  T  W  S  I  A  D  K  R  V  E   38

121  AAATTGGCCTCTGATGCAGTCTCCTTGGCCTACACTAAGTATAAGCACTCTTTATCTCCT  180
 39     N  W  P  L  M  Q  S  P  W  P  T  L  S  I  S  T  L  Y  L  L   58

181  GTTTGTGTGGCTGGGTCCAAAATGGATGAAGGACCGAGAACCTTTTCAGATGCGTCTAGT  240
 59     F  V  W  L  G  P  K  W  M  K  D  R  E  P  F  Q  M  R  L  V   78

241  GCTCATTATCTATAATTTTGGGATGGTTTTGCTTAACCTCTTTATCTTCAGAGAGTTATT  300
 79     L  I  I  Y  N  F  G  M  V  L  L  N  L  F  I  F  R  E  L  F   98

301  CATGGGATCATATAATGCGGGATATAGCTATATTTGCCAGAGTGTGGATTATTCTAATAA  360
 99     M  G  S  Y  N  A  G  Y  S  Y  I  C  Q  S  V  D  Y  S  N  N  118

361  TGTTCATGAAGTCAGGATAGCTGCTGCTCTGTGGTGGTACTTTGTATCTAAAGGAGTTGA  420
119     V  H  E  V  R  I  A  A  A  L  W  W  Y  F  V  S  K  G  V  E  138

421  GTATTTGGACACAGTGTTTTTTATTCTGAGAAAGAAAAACAACCAAGTTTCTTTCCTTCA  480
139     Y  L  D  T  V  F  F  I  L  R  K  K  N  N  Q  V  S  F  L  H  158

481  TGTGTATCATCACTGTACGATGTTTACCTTGTGGTGGATTGGAATTAAGTGGGTTGCAGG  540
159     V  Y  H  H  C  T  M  F  T  L  W  W  I  G  I  K  W  V  A  G  178

541  AGGACAAGCATTTTTTGGAGCCCAGTTGAATTCCTTTATCCATGTGATTATGTACTCATA  600
179     G  Q  A  F  F  G  A  Q  L  N  S  F  I  H  V  I  M  Y  S  Y  198

601  CTATGGGTTAACTGCATTTGGCCCATGGATTCAGAAATATCTTTGGTGGAAACGATACCT  660
199     Y  G  L  T  A  F  G  P  W  I  Q  K  Y  L  W  W  K  R  Y  L  218

661  GACTATGTTGCAACTGATTCAATTCCATGTGACCATTGGGCACACGGCACTGTCTCTTTA  720
219     T  M  L  Q  L  I  Q  F  H  V  T  I  G  H  T  A  L  S  L  Y  238

721  CACTGACTGCCCCTTCCCCAAATGGATGCACTGGGCTCTAATTGCCTATGCAATCAGCTT  780
239     T  D  C  P  F  P  K  W  M  H  W  A  L  I  A  Y  A  I  S  F  258

781  CATATTTCTCTTTCTTCTACATTCGGACATACAAAGAGCCTAAGAAACCAAAAGCTGGAA  840
259     I  F  L  F  L  L  H  S  D  I  Q  R  A  *                    272

841  AAACAGCCATGAATGGTATTTCAGCAAATGGTGTGAGCAAATCAGAAAAACAACTCATGA  900

901  TAGAAAATGGAAAAAAGCAGAAAAATGGAAAAGCAAAAGGAGATTAAATTGAACTGGGCC  960

961  TTAACTG  967
```

FIG.4

Mouse ELF protein
(SEQ.ID.NO. 5)

| | |
|---|---|
| 0-40 | MGLLDSEPGSVLNAMSTAFNDTVEFYRWTWTIADKRVADW |
| 41-80 | PLMQSPWPTISISTLYLLFVWLGPKWMKDREPFQMRLVLI |
| 81-120 | IYNFGMVLLNLFIFRELFMGSYNAGYSYICQSVDYSNDVN |
| 121-160 | EVRIAAALWWYFVSKGVEYLDTVFFILRKKNNQVSFLHVY |
| 161-200 | HHCTMFTLWWIGIKWVAGGQAFFGAQMNSFIHVIMYSYYG |
| 200-240 | LTAFGPWIQKYLWWKRYLTMLQLVQFHVTIGHTALSLYTD |
| 240-280 | CPFPKWMHWALIAYAISFIFLFL*NFYTR*TYNEPKQSKTGK |
| 280-313 | *TATNGISSNGVNKSEKALENGKPQKNGKPKGE* |

FIG.5

Mouse *elf* cDNA (SEQ.ID.NO. 6) and
Amino acids (SEQ.ID.NO.5)

```
  1 CAGTCGCCCACGGTCCATCGGAGCCTCTCTTCTCGCCCGCTTGTCGTACCTCTCCTCGCC   60

61 AAGATGGGGCTGCTGGACTCAGAGCCCGGCAGCGTCCTGAACGCGATGTCCACGGCATTC  120
  1     M  G  L  L  D  S  E  P  G  S  V  L  N  A  M  S  T  A  F   19

121 AACGACACCGTGGAGTTCTATCGCTGGACCTGGACCATTGCAGATAAACGTGTAGCAGAC  180
 20  N  D  T  V  E  F  Y  R  W  T  W  T  I  A  D  K  R  V  A  D   39

181 TGGCCGCTGATGCAGTCTCCATGGCCAACGATAAGCATAAGCACGCTCTATCTCCTGTTC  240
 40  W  P  L  M  Q  S  P  W  P  T  I  S  I  S  T  L  Y  L  L  F   59

241 GTGTGGCTGGGTCCAAAGTGGATGAAAGACCGCGAGCCGTTCCAAATGCGCTTAGTACTC  300
 60  V  W  L  G  P  K  W  M  K  D  R  E  P  F  Q  M  R  L  V  L   79

301 ATAATCTATAATTTTGGCATGGTTTTGCTTAACCTTTTCATCTTCAGAGAGCTATTCATG  360
 80  I  I  Y  N  F  G  M  V  L  L  N  L  F  I  F  R  E  L  F  M   99

361 GGATCATACAACGCAGGATACAGCTATATTTGCCAGTCAGTGGATTATTCTAATGATGTT  420
100  G  S  Y  N  A  G  Y  S  Y  I  C  Q  S  V  D  Y  S  N  D  V  119

421 AATGAAGTCAGGATAGCGGCGGCCCTGTGGTGGTATTTTGTATCGAAAGGCGTTGAGTAT  480
120  N  E  V  R  I  A  A  A  L  W  W  Y  F  V  S  K  G  V  E  Y  139

481 TTGGACACAGTGTTTTTTATCCTGAGGAAGAAAAACAACCAAGTCTCCTTCCTTCACGTG  540
140  L  D  T  V  F  F  I  L  R  K  K  N  N  Q  V  S  F  L  H  V  159

541 TACCACCACTGCACCATGTTCACTCTGTGGTGGATTGGAATCAAGTGGGTGGCTGGAGGC  600
160  Y  H  H  C  T  M  F  T  L  W  W  I  G  I  K  W  V  A  G  G  179

601 CAAGCGTTTTTCGGGGCCCAGATGAACTCTTTCATCCACGTGATCATGTACTCCTACTAT  660
180  Q  A  F  F  G  A  Q  M  N  S  F  I  H  V  I  M  Y  S  Y  Y  199

661 GGGCTGACTGCGTTCGGCCCCTGGATCCAGAAATATCTTTGGTGGAAGCGATACCTGACC  720
200  G  L  T  A  F  G  P  W  I  Q  K  Y  L  W  W  K  R  Y  L  T  219
```

FIG.6A

```
721  ATGCTGCAGCTGGTCCAGTTCCACGTGACCATCGGACACACAGCACTGTCTCTCTACACC  780
220   M   L   Q   L   V   Q   F   H   V   T   I   G   H   T   A   L   S   L   Y   T   239

781  GACTGCCCCTTCCCCAAGTGGATGCACTGGGCTCTGATCGCCTACGCCATCAGCTTCATC  840
240   D   C   P   F   P   K   W   M   H   W   A   L   I   A   Y   A   I   S   F   I   259

841  TTCCTCTTCCTCAACTTCTACACTCGGACATACAATGAGCCGAAGCAGTCAAAAACCGGA  900
260   F   L   F   L   N   F   Y   T   R   T   Y   N   E   P   K   Q   S   K   T   G   279

901  AAGACGGCCACGAATGGTATCTCATCGAACGGCGTGAATAAATCAGAGAAAGCGTTAGAA  960
280   K   T   A   T   N   G   I   S   S   N   G   V   N   K   S   E   K   A   L   E   299

961  AACGGGAAACCCCAGAAAAACGGGAAGCCAAAAGGAGAGTAAATTGAACTGGGCCTTAAC  1020
300   N   G   K   P   Q   K   N   G   K   P   K   G   E   *                              313

1021 CGGTAGACAGTGAGGAAACTCCTGTGTCATTTTAAAAAGTTCAGGGGCAACAGAAGCAGA  1080

1081 GGGTCTGGGCTGGGGAGAAAGGCAGATAGGGTCTTTGCCCTTCAGACTGAGTAAAACTTT  1140

1141 TCAATATATGGTACCCAGATGTTTTATTTATGAAGTTTTTATTTTAAAAGTTTTTTTTTT  1200

1201 ATTAACCCTTCATGTTGTCCAAAACCAAAGCAACCCCCAATGTGGACCTTGGGAGCCTTT  1260

1261 TCTCTGTTAACATTCCGCCTTGGGCAATGGGG  1292
```

FIG.6B

Human *ELF* gene:Genomic DNA
SEQ.ID.NO. 7

```
   1  GCCGCCACCG CCTCCGGGGT CAGCCCTCTC TCTGGGTCTC CGCTTTCTCC
  51  TGCCGCCAGC GCCCGCTCAT CGCCGCGATG GGGCTCCTGG ACTCGGAGCC     ┐
 101  GGGTAGTGTC CTAAACGTAG TGTCCACGGC ACTCAACGAC ACGGTAGAGT     │ Exon 1
 151  TCTACCGCTG GACCTGGTCC ATCGCAGgta aagccgctga cttccccatc     ┘
 201  ctcgctcggt ccccgcggg gggtcaccgg ccctggtct cgcagctccc
 251  gggcccggcc ccacaggccc ccgcgccctg cggctttcgg atgctgcgga
 301  nnnnnnnnnn agccacttgc aggagtcagt attgtttctt tggttttttat
 351  accatgtatt ttttgttggg actcaaagga cagtgatccg tatttagtca
 401  aattaggaaa ttaagttgaa acatcttgat tcctaaaaag tgtattttat
 451  aaaacattta ctgattaatg aattttatgg tattttgttc tctctatagA     ┐
 501  TAAGCGTGTG GAAAATTGGC CTCTGATGCA GTCTCCTTGG CCTACACTAA     │
 551  GTATAAGCAC TCTTTATCTC CTGTTTGTGT GGCTGGGTCC AAAATGGATG     │ Exon 2
 601  AAGGACCGAG AACCTTTTCA GATGCGTCTA GTGCTCATTA TCTATAATTT     │
 651  TGGGATGGTT TTGCTTAACC TCTTTATCTT CAGAGAGgta tgttttttaag    ┘
 701  atcactttaa taattttcca aggttattgg aaatttaaaa atgagaatgt
 751  gtaaaaccat nnnnnnnnnn aatcggaatg catgaaattt ttaatgcatt
 801  tgaaattttt aagaaaata ttgtgtttaa ataatttga aaggctacat
 851  tttgtatata attgtgtttt taatgctgtg tttactaaaa ctttactaca
 901  aatattatta ctcttttcc agTTATTCAT GGGATCATAT AATGCGGGAT      ┐
 951  ATAGCTATAT TTGCCAGAGT GTGGATTATT CTAATAATGT TCATGAAGTC     │ Exon 3
1001  AGGgtaagta cattaaaaat actcttaatc agtaaaagtg gtttgatttt    ┘
1051  tataggcccc agtctgtgaa aannnnnnnn nntccatgcc ttgtacattt
1101  tgtgcaatat acaaatgttt attttggast tacttacaat gagtataaac
1151  ccatacaata gtgtcatttt ggtgtttata acacgctttc ccttttttaca
1201  gATAGCTGCT GCTCTGTGGT GGTACTTTGT ATCTAAAGGA GTTGAGTATT    ┐
1251  TGGACACAGT GTTTTTATT CTGAGAAAGA AAAACAACCA AGTTTCTTTC     │
1301  CTTCATGTGT ATCATCACTG TACGATGTTT ACCTTGTGG GGATTGGAAT    │ Exon 4
1351  TAAGTGGGTT GCAGGAGGAC AAGgtgagca ttttcaggaa tatactgctt    ┘
1401  gcgtttaatt gcatatatgt gttcagtgga aagcaatgag aacctaggac
1451  tttgacttga tctaccattt aacttgcttt catggttaat catttccatg
1501  ttcatttctt ttttttttt tttttttttt ttttgagatg gagtctcgct
1551  ctgtcaccag gctggagtgc agtggcgcga tctcggctca ctgcaacctc
1601  cacctcccgg gttccagcga ttctcctgcc tcagcctcct gagtagctgg
1651  gactacaggc acacaccacc acgcctagct aatttttgt attttagta
1701  gagacagggt ttcaccatgt tggccaggat ggtaaaagat ctcttgacct
1751  tgtgatccgc nnnnnnnnnn catctcagtg gcttactgcc taataaaatt
1801  ttctgtatct tgtaattacc tgttgttttt ctaaagCATT TTTTGGAGCC     ┐
1851  CAGTTGAATT CCTTTATCCA TGTGATTATG TACTCATACT ATGGGTTAAC     │
1901  TGCATTTGGC CCATGGATTC AGAAATATCT TGGTGGAAA CGATACCTGA     │ Exon 5
1951  CTATGTTGCA ACTgtgagt taaatgcttc caaagtttct tctggtaaaa      ┘
2001  tactgaaatt gtttaaattt gattaatttt aaagtgcaat gtcattttag
2051  acaatttcn nnnnnnnnna gatgcgatg ttgttaaaag ttgtttacta
2101  ttcagattaa atgttttgtg ctgtcatttc tgttttcag ATTCAATTCC     ┐
2151  ATGTGACCAT TGGCACACG GCACTGTCTC TTTACACTGA CTGCCCCTTC    │
2201  CCCAAATGGA TGCACTGGGC TCTAATTGCC TATGCAATCA GCTTCATATT    │
2251  TCTCTTTCTT AACTTCTACA TTCGGACATA CAAAGAGCCT AAGAAACCAA    │ Exon 6
2301  AAGCTGGAAA AACAGCCATG AATGGTATTT CAGCAAATGG TGTGAGCAAA    │
2351  TCAGAAAAAC AACTCATGAT AGAAAATGGA AAAAGCAGA AAAATGGAAA     │
2401  AGCAAAAGGA GATTAAATTG AACTGGGCCT TAACTGTTGT TGACA          ┘
```

FIG.7

Human (SEQ.ID.NO.1) and mouse ELF (SEQ.ID.NO.5)

```
Human_ELF  MGLLDSEPGSVLNVVSTALNDTVEFYRWTWSIADKRVENWPLMQSPWPTLSISTLYLLFV
Mouse_ELF  MGLLDSEPGSVLNAMSTAFNDTVEFYRWTWIIADKRVADWPLMQSPWPTISISTLYLLFV Human_ELF  WLGPKWMKDREPFQMRLVLIIYNFGMVLLNLFIFRELFMGSYNAGYSYICQSVDYSNNVH
Mouse_ELF  WLGPKWMKDREPFQMRLVLIIYNFGMVLLNLFIFRELFMGSYNAGYSYICQSVDYSNDVN Human_ELF  EVRIAAALWWYFVSKGVEYLDTVFFILRKKNNQVSFLHVYHHCTMFTLWWIGIKWVAGGQ
Mouse_ELF  EVRIAAALWWYFVSKGVEYLDTVFFILRKKNNQVSFLHVYHHCTMFTLWWIGIKWVAGGQ Human_ELF  AFFGAQLNSFIHVIMYSYYGLTAFGPWIQKYLWMKRYLTMLQLIQFHVTIGHTALSLYTD
Mouse_ELF  AFFGAQMNSFIHVIMYSYYGLTAFGPWIQKYLWMKRYLTMLQLVQFHVTIGHTALSLYTD Human_ELF  CPFPKWMHWALIAYAISFIFLFLNFYIRTYKEPKKPKAGKTAMNGISANGVSKSEKQLMI
Mouse_ELF  CPFPKWMHWALIAYAISFIFLFLNFYTRTYNEPKQSKTGKTATNGISSNGVNKSEKAL..

Human_ELF  ENGKKQKNGKAKGD
Mouse_ELF  ENGKPQKNGKPKGE
```

FIG.8

Human ELF (SEQ.ID.NO.1) and yeast Elo2 (SEQ.ID.NO.8) and Elo3 (SEQ.ID.NO.9)

```
YeastElo2   MN...S.......LVTQYAAPLFERYP.....QLHDYLPTLERPFFNISLWEHFDDVVTR
YeastElo3   MNTTTS.......TVIAAVADQFQSLNSSSSCFLKVHVPSIENPFG.IELWPIFSKVFEY
Human_ELF   MGLLDSEPGSVLNVVSTALNDTVEFYR................WTWSIADKRVEN YeastElo2   VTNGRFVPSE.FQFIAGELPLSTLP.PVLYAITAYYVIIFGG....RFL.LSKSKPFKLN
YeastElo3   FS.G..YPAEQFEFIHNKTFLANGY.HAVSIIIVYYIIIFGGQAILRALNASPLK.FKL.
Human_ELF   ......WP...........LMQSPWPTLSISTLYLLFVWLG..........PKWMKDR YeastElo2   GLFQLHNLVLTSLSLTLLLLMVEQLVPIIVQH.GLYFA....ICNIGAWTQPLVTLYYMN
YeastElo3   .LFEIHNLFLTSISLVLWLLMLEQLVP.MVYHNGLFWS.....ICSKEAFAPKLVTLYYLN
Human_ELF   EPFQMR.LVLIIYNFGMVLLN...LFIFRELFMGSYNAGYSYICQS.......V..DYSN YeastElo2   ............YIV.KFIEFIDTFFLVLKHKK...LLFLHTYHHGATALLCYTQLMGT
YeastElo3   ............YLT.KFVELIDTVFLVLRRKK...LLFLHTYHHGATALLCYTQLIGR
Human_ELF   NVHEVRIAAALWWYFVSKGVEYLDTVFFILR.KKNNQVSFLHVYHHCTMFTLWW...IG.

YeastElo2   TSISWVP.......ISLNLGVHVVMYWYYFLAARG...IR..VWWKEWVTRFQIIQFVLDI
YeastElo3   TSVEWVV.......ILLNLGVHVIMYWYYFLSSCG...IR..VWWKQWVTRFQIIQFLIDL
Human_ELF   ..IKWVAGGQAFFGAQLNSFIHVIMYSYYGLIAFGPWIQKYLWWKRYLTMLQLIQFHVTI YeastElo2   GFIYFAVYQKAVHLYFP.ILPHCGDCVGSTTATFA.GCAIISSYLVLFISFYINVYK...
YeastElo3   VFVYFATYTFYAHKYLDGILPNKGTCYG.TQAAAAYGYLILTSYLLLFISFYIQSYK...
Human_ELF   G.......HTALSLYTDCPFP.....KWMHWALIA..YAI..SFIFLFLNFYIRTYKEPK YeastElo2   ..RKGTKTSRVVKR...AHGGVAAKVNEYVN.....VDLKNVPTPSPSPKPQHRRKR.
YeastElo3   ..KGGKKT..VKKESEVSGSVASGSSTGV........KTSNTKVSS......RK..
Human_ELF   KPKAG.KT.......AMNGISANGVSKSEKQLMIENGKKQKNGK..........AKGD
```

FIG.9

IN SITU HYBRIDIZATION OF THE HUMAN
ELF PROBE TO THE RHESUS MONKEY RETINA

SENSE

GCL
IPL
INL
OPL
ONL
IS
OS
RPE

IN SITU HYBRIDIZATION OF THE HUMAN
ELF PROBE TO THE RHESUS MONKEY RETINA

ANTISENSE

Promoter region of the human ELF gene

```
   1 ACTTAAGTTG ACCTCCACGG TAGAAGAAAT ACCAGGGAAA TACCTGAAGC
  51 TGTTTTAACA ATTTCTCCTT GTATTAAGTA TTATGCTGCA GTTTTGCGTG
 101 TGTGAATGGA AGTATGGGTA GAGATCTGTT CTCCCTAAAA ACTCCAGGAT
 151 TCCACAATAT AGAAATAGTA ATCAAATTTT TAGGTGAAGC TCGAACTAAT
 201 CCGAACTTTG TTAGATCATC ACTGTAAATG AATGGGTATT TATCCACTCC
 251 CTAAATGAAG AGACTTGACT GGATTTCTTT TTTTTATATA GCTACTAGAA
 301 TCTGTTACAC ATAATTTAGG ATTGAGACTT GAGAAATTGT CATTCCAATC
 351 CAGAAAACTT TAGATTTGCA AATATATTTG ACAAATTAAT AAATTAACAT
 401 TTTATTTGGT TAATTTCAAG AATAGGGCAT TTAAAGAAGT CTGTGTTTGC
 451 TTTAGTTCGG CAATAAAGTT CCTGCCACTC ACAATAATCC TTATTATTCT
 501 CTGAAAGACA TGTTATATTT TTGTCATCAT AAATATTTAT TAATTACTGT
 551 TTATAGCACT GGGTTAGGTA CTCATCAAGC AACCAAAAAT AATTCTTACC
 601 ATCTAGGATG CTTCCAATAT AAAATATAGA CAATATATAA CCAGGTCAAT
 651 TGGGAAATAG ATCATTTCAG TATGATAAAA GATAGTATTC ACATTAACAG
 701 TGTGAAAGGG CAGGAACAAT AAGACACTTG ACTCACTGGT CTTTAAAATG
 751 TAGCATCCAA AATGAGCAAG TGGAGAAAAG GTTAAACAAG TAGGTGACAC
 801 ATTTAAAAAA CAAGTAGATG AAAGGACTAT TCTCAAAAAT CTTGTTTTAT
 851 GTGAGAAACC ATCAAATTAT GAATTCCAAG TACTGTATTT TTTTTACTTT
 901 TCAAGGGTAG GCTCTCCTAT ACCTTATCTA AACAATTTTT CAAAATAGCC
 951 ACAATTACTT TGTTTTCCTC TCTACACTAA ATTGCCCTTT GCCTCTTGAG
1001 CGATTATCTT TTTCAGATTC ACCTCAACTT CTTCAGGTTC AAGCGGACTT
1051 CACCTGTAAG CCCCTCTCGG TTCTCCCTCT TCTCTGAACT ACTAATGGCC
1101 TAATTTAGCA CAATTATATT GCTTTGTTCA TTCCATGTAT AGTAAAAGAG
1151 TCTACAAAAC ACATGCAAGC ATTCATGCAA TTATATGTTG ATTTGTTCAT
1201 GGGTCGACCC CAAAGTCTAT TCTCCATCGC TGAAGCATGG AAGACAAATA
1251 CCCTTCACTT CTTCAGAGGC ATAACACATG CACTTCTCTT GTCATGGTGA
1301 CAGGCATGTG CTGGTGGAGG TCAAAGAAAC AGGAACACAA GTGAAATCGA
1351 GGTGAGTGTC AGGTAAGGAC CAAAGCACCA CGCCTACCTC ATCTTTGCCC
1401 ACAGAACACC CATTCTTCCC GTGTCCTGTT TCCAGGACG TATCCGGGGC
1451 GGATAAGAAA TCACCCGTGG GGAGGCGGTG AACTCCTCCG CAGGGGCCGA
1501 TGCCCGGGAC AGGGGCGGGG AAGGCTAATG AGGCGACTTG TGCGGGGAGG
1551 GGCCAAGGAG GAGCCCAGGT GTCCCGCTCC CGCTCGACGG CGCGCGCCTG
1601 CGCGAGCCCA GTTGGCGTCG CACCCTTGAG CGCAGCATCC CTACGCCAGC
1651 GAGTCCCAAT ACTAGGGAGG GAGGGAGGGA GGAGGGGCGG CCGGCCCCCC
1701 GCCCCGCGC GCGGCCACGT GACGCCGGCT GAGGAGATTG GAGGGGCGGC
1801 CTCCACCTCC TCGTCTTTCT CCCGGGAACC TTGACGACGC CTTCCGCTTG
1851 GCCCTGCCTT CTGCCGCATC CCGCCGCCG CGGCGCCTTG AGGAGCAGGA
1901 GAAGACGCAG CCGGGCCGCC GCCGTTAGAG GGGTTCCCGG CCGCCGCTCG
1951 CCCCGTCGGC CGCCACCGCC TCCGGGGTCA GCCCTCTCTC TGGGTCTCCG
2001 CTTTCTCCTG CCGCCAGCGC CGCTCATCG CCGCGATG
```

FIG.16

GENE RESPONSIBLE FOR STARGARDT-LIKE DOMINANT MACULAR DYSTROPHY

This application is a divisional of 10/276,732, filed Oct. 3, 2003 now U.S. Pat. No. 7,091,005, which claims the benefit of U.S. Provisional Application No. 60/204,990, filed May 16, 2000.

FIELD OF THE INVENTION

This invention relates to the gene responsible for causing Stargardt-like dominant macular dystrophy, and to assays which use this gene or the protein encoded by it, and to methods of treating this condition by administering the protein.

BACKGROUND

Macular dystrophy is a term applied to a heterogeneous group of diseases that collectively are the cause of severe visual loss in a large number of people. A common characteristic of macular dystrophy is a progressive loss of central vision resulting from the degeneration of photoreceptor cells in the retinal macula. In many forms of macular dystrophy, the end stage of the disease results in legal blindness. More than 20 types of macular dystrophy are known: e.g., age-related macular dystrophy, Stargardt-like dominant macular dystrophy, recessive Stargardt's disease, atypical vitelliform macular dystrophy (VMD1), Usher Syndrome Type 1B, autosomal dominant neovascular inflammatory vitreoretinopathy, familial exudative vitreoretinopathy, and Best's macular dystrophy (also known as hereditary macular dystrophy or Best's vitelliform macular dystrophy (VMD2). For a review of the macular dystrophies, see Sullivan & Daiger, 1996, *Mol. Med. Today* 2:380–386.

Stargardt-like dominant macular dystrophy (also called autosomal dominant macular atrophy) is a juvenile-onset macular degeneration. Patients afflicted with this disease generally have normal vision as young children, but during childhood, visual loss begins, which rapidly progresses to legal blindness. Clinically it is characterized by the presence of an atrophic macular lesion with sharp borders and is often associated with yellow fundus flecks. The pathological features seen in Stargardt-like dominant macular dystrophy are in many ways similar to the features seen in age-related macular dystrophy (AMD), the leading cause of blindness in older patients in the developed world.

AMD is an extraordinarily difficult disease to study genetically, since by the time patients are diagnosed, their parents are usually no longer living and their children are still asymptomatic. Thus, family studies which have led to the discovery of the genetic basis of many other diseases have not been practical for age-related macular dystrophy. As there are currently no widely effective treatments for AMD, it is hoped that study of Stargardt-like dominant macular dystrophy, and in particular the discovery of the underlying genetic cause of Stargardt-like dominant macular dystrophy, will shed light on age-related macular dystrophy as well. A significant proportion of the AMD cases is caused by recessive mutations in the recessive Stargardt disease gene. (Allikmets, et al 1997 *Science* 277:1805–1807).

It seems reasonable to suggest that mutations within the disease gene responsible for Stargardt-like dominant macular dystrophy which closely resembles the recessive Stargardt disease may be responsible for the significant proportion of AMD cases. It would be desirable to characterize the gene responsible for this disease in order to have a better understanding of this disease and to elucidate its potential role in other forms of macular degeneration.

DETAILED DESCRIPITON OF THE INVENTION

In accordance with this invention, a mutant gene responsible for autosomal dominant Stargardt-like macular dystrophy has been identified and sequenced. Additionally, the normal allelic form of this gene has also been identified and sequenced.

A new gene, presently designated "ELF" (for Elongation of Fatty Acids), is potentially involved in the elongation pathway for the synthesis of decosahexaenoic fatty acid (DHA), a critical component in retinas. The mutant version of this gene contains a 5-base pair deletion which causes a frameshift mutation. The resultant mutated protein does not function in the DHA pathway, resulting in retinal dysfunction.

Thus one aspect of this invention is a nucleic acid encoding the normal form of ELF protein, which is free from associated nucleic acids. In preferred embodiments, the nucleic acid sequence is a DNA, and in more preferred embodiments it is a cDNA.

Another aspect of this invention is a nucleic acid encoding a mutant form of ELF, which is free from associated nucleic acids. In preferred embodiments, the nucleic acid is a DNA, and in more preferred embodiments, it is a cDNA.

Another aspect of this invention are the novel proteins, normal ELF and its mutant form, free from associated proteins. Also part of this invention are fragments of these proteins which retain at least one biological activity.

A further aspect for this invention is a method of treating individuals who suffer from Stargardt-like macular dystrophy comprising administering to the individual an effective amount of ELF protein. The ELF protein may be in a pharmaceutically acceptable carrier, and it may be administered in the form of eyedrops or other ophthalmic preparation.

Another aspect of this invention is a method of treating individuals who suffer from Stargardt-like macular dystrophy comprising introducing a nucleic acid encoding the ELF protein into the individual. This gene therapy approach may involve the use of viral vectors, such as adenovirus, or it may involve the use of plasmid DNA.

Yet another aspect of this invention are assays to identify if an individual is at risk for Stargardt-like macular dystrophy comprising determining if the individual's DNA contains a gene for a mutant form of ELF.

Another aspect of this invention is the use of ELF gene's 5' regulatory region for targeting the expression of genes specifically to photoreceptor cells of the retina for gene therapy of macular degeneration.

Another aspect of this invention is the use of mouse ELF DNA or mouse ELF protein corresponding to the normal or mutant form of human ELF for generating an animal model (knock-out or transgenic) that can be used for testing the anti-AMD compounds.

A further aspect of this invention are methods of producing long chain fatty acids using DNA encoding ELF or using ELF protein.

BRIEF DESCRIPTION OF THE DRAWINGS

FIG. 1 is the protein for normal human ELF protein (SEQ.ID.NO. 1). The underlined amino acids represent 5 putative transmembrane segments. The HXXHH motif between predicted membrane spanning regions 2 and 3 that is characteristic of dioxy iron cluster proteins is double underlined. The protein fragment deleted in patients with Stargardt-like macular dystrophy is shown in italics. The cytosolic carboxy-terminal dilysine motif responsible for the retrieval of trans-membrane proteins from cis-Golgi to the endoplasmic reticulum is shown in bold italics.

Figure 10:
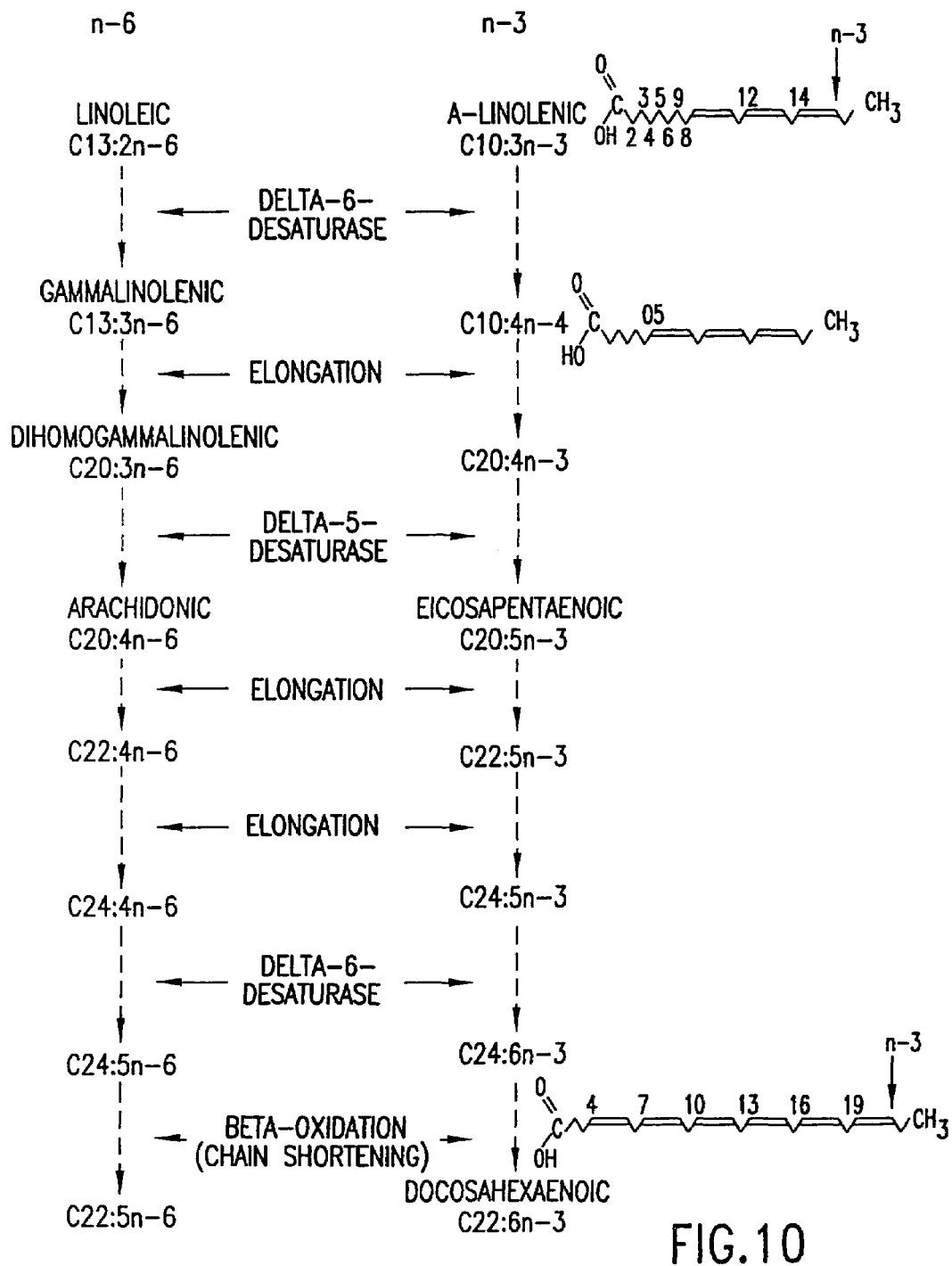

FIG. 2 is the protein for mutant human ELF protein which causes Stargardt-like dominant macular dystrophy (SEQ.ID.NO. 2). Underlined amino acids represent four of five putative transmembrane segments; the fragment of the fifth transmembrane segment that is common for normal and mutant alleles of the protein is highlighted by the dotted line. The HXXHH motif between predicted membrane spanning regions 2 and 3 that is characteristic of dioxy iron cluster proteins is double underlined. The protein fragment generated by the 5-bp deletion in patients with Stargardt-like macular dystrophy is shown in italics.

FIG. 3 is normal human ELF cDNA (SEQ.ID.NO. 3) and the amino acid sequence (SEQ.ID.NO.1) of the human ELF protein. Underlined nucleotides in bold encompassing base pairs 797–801 represent the deletion found in patients with dominant Stargardt-like macular dystrophy. The protein fragment deleted in patients with Stargardt-like macular dystrophy is shown in bold underline FIG. 4 is mutant human ELF cDNA (SEQ.ID.NO. 4) and the amino acid sequence (SEQ.ID.NO. 2) of the human mutant ELF protein. The region of the protein encompassing amino acids 264–271 (bold underlined) represent a fragment generated as a result of the 5-base pair deletion in patients with dominant Stargardt-like macular dystrophy.

FIG. 5 is the protein for normal mouse ELF protein (SEQ.ID.NO. 5). Underlined amino acids represent 5 putative transmembrane segments. The HXXHH motif between predicted membrane spanning regions 2 and 3 that is characteristic of dioxy iron cluster proteins is double underlined. The protein fragment similar to the human ELF fragment deleted in patients with Stargardt-like macular dystrophy is shown in italics. Cytosolic carboxy-terminal dilysine motif responsible for the retrieval of transmembrane proteins from cis-Golgi to the endoplasmic reticulum is shown in bold italics.

FIG. 6 is mouse cDNA for ELF (SEQ.ID.NOS. 6) and the amino acid sequence (SEQ.ID.NO.:5) of the mouse ELF protein.

FIG. 7 shows the genomic DNA sequence of the ELF gene (SEQ.ID.NO.:8). Underlined nucleotides in capitals represent exons. Initiating ATG codon in exon 1 and terminating TAA codon in exon 6 are shown in bold italics. The exact lengths of the gaps between the exons are unknown; these gaps are presented as runs of ten bold n as a convenience only.

FIG. 8 shows the pairwise comparison of human and mouse ELF proteins. The upper amino acid sequence shown is the human ELF protein (SEQ.ID.NO. 1). The lower amino acid sequence shown is the mouse ELF protein (SEQ.ID.NO. 5). The two proteins are highly identical which indicates they are true orthologues. Both proteins share the cytosolic carboxy-terminal dilysine motif responsible for the retrieval of transmembrane proteins from cis-Golgi to the endoplasmic reticulum (two lysines are located at −3 and −5 positions with respect to the carboxyl terminus).

FIG. 9 depicts the sequence alignment of the human ELF protein (SEQ.ID.NO. 1) and its two yeast homologues, Elo2p (SEQ.ID.NO. 8) and Elo3p (SEQ.ID.NO. 9) from Oh et al.,1997 *J. Biol. Chem* 272:17376–17384. The degree of homology is high enough to assign the function of elongation of fatty acids to the human ELF protein.

Figure 11:
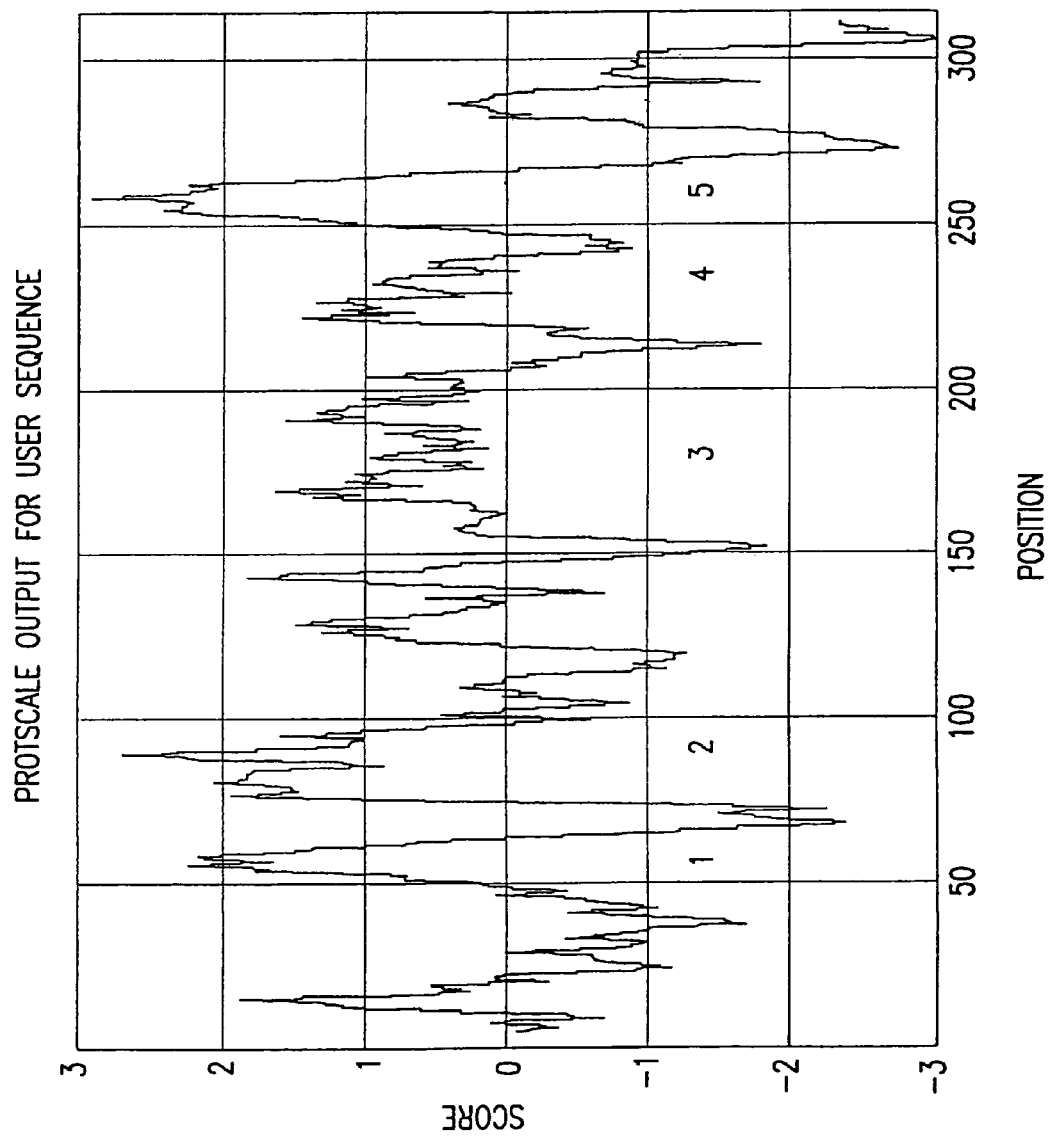

FIG. 10 depicts the enzymatic conversions involved in the linoleic acid (n-3) and alpha-linolenic acid (n-6) pathways of essential fatty acid synthesis, including three elongation steps required of the biosynthesis of DHA FIG. 11 shows a Kyte-Doolittle hydropathy plot of human ELF. Numbers 1 to 5 mark putative transmembrane segments. The hydropathy plot and membrane topology of human ELF (SEQ.ID.NO. 1) are similar to those proposed for its two yeast homologues, Elo2p (SEQ.ID.NO. 8) and Elo3p (SEQ.ID.NO. 9), experimentally shown to be involved in elongation of fatty acids.

Figure 12:
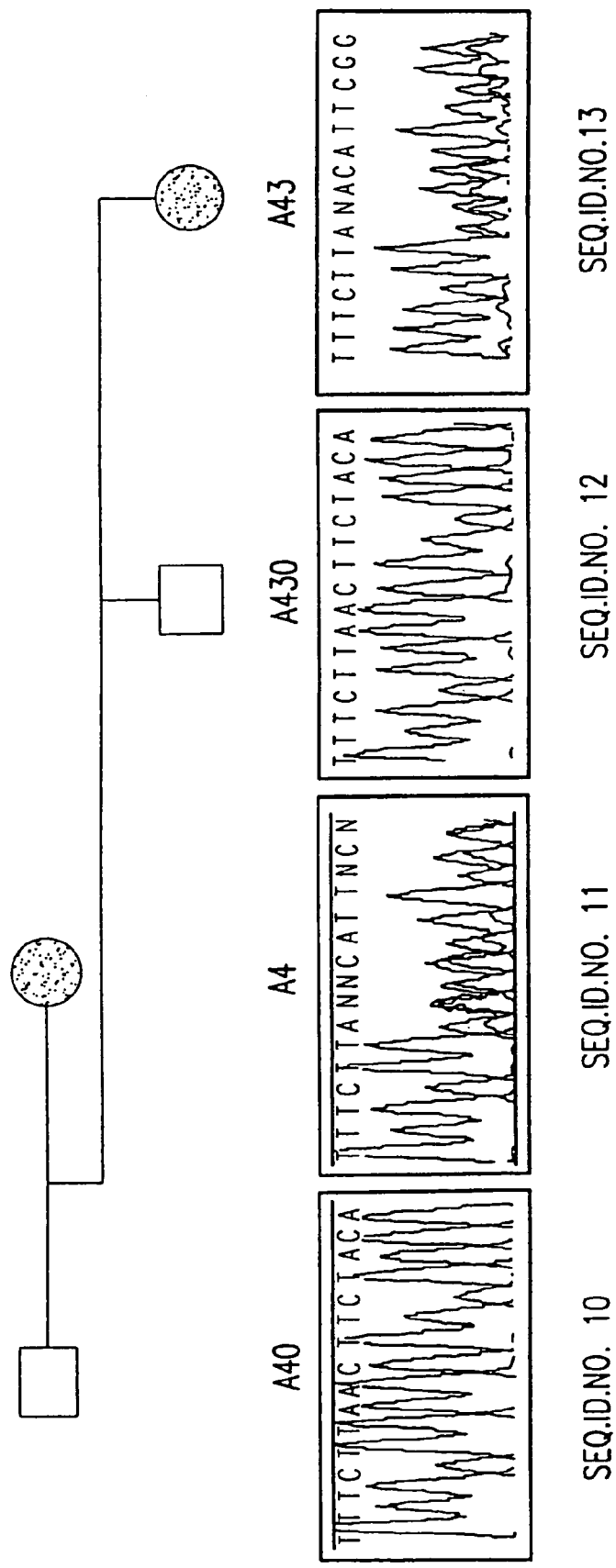

FIG. 12 shows association (segregation) of the 5 base pair deletion within the ELF gene with the disease phenotype in the family with dominant Stargardt-like macular dystrophy. The figure shows the structure of this pedigree and four sequencing runs (boxed) of PCR fragments that represent exon 6 and adjacent intronic regions of the human ELF gene (SEQ.ID.NOS.:10, 11, 12, and 13). From left to right, the runs are from A40 (father, unaffected with Stargardt-like dominant macular dystrophy), A4 (mother, affected with Stargardt-like dominant macular dystrophy), A430 (son of A4 and A40, unaffected with Stargardt-like dominant macular dystrophy), A43 (daughter of A4 and A40, affected with Stargardt-like dominant macular dystrophy). Reading the boxed chromatograms from left to right, the 5-base pair deletion shows up as appearance of double peaks starting from position 7 in the case of patients A4 and A43.

Figure 13B:
Figure 13A:
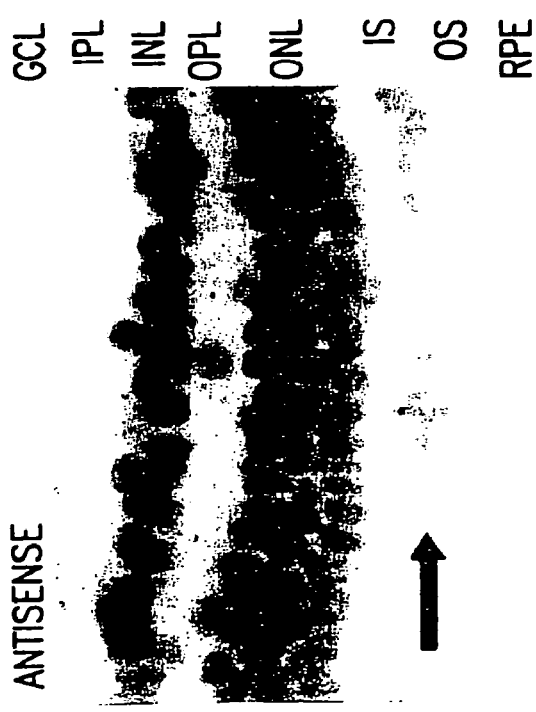

FIGS. 13A and 13B show the result of in situ hybridization of the human ELF mRNA in rhesus monkey retina. FIG. 13A shows specific expression in the inner segments of photoreceptor cells with the antisense probe. Probe signal is indicated by the arrow; retinal layers are visualized with propidium iodide counterstain. FIG. 13B shows the hybridization with the sense control probe (sense probe is not complementary to the ELF mRNA). Retinal layers are marked as RPE, retinal pigment epithelium; OS, outer segments of photoreceptors; IS, inner segments of photoreceptors; ONL, outer nuclear layer; OPL, outer plexiform layer; INL, inner nuclear layer; IPL, inner plexiform layer; GCL, ganglion cell layer. PhumGL1/HR2 is a hybridization probe that represents a fragment of the human normal ELF cDNA (SEQ.ID.NO. 4). with coordinates 561–771.

Figure 14:
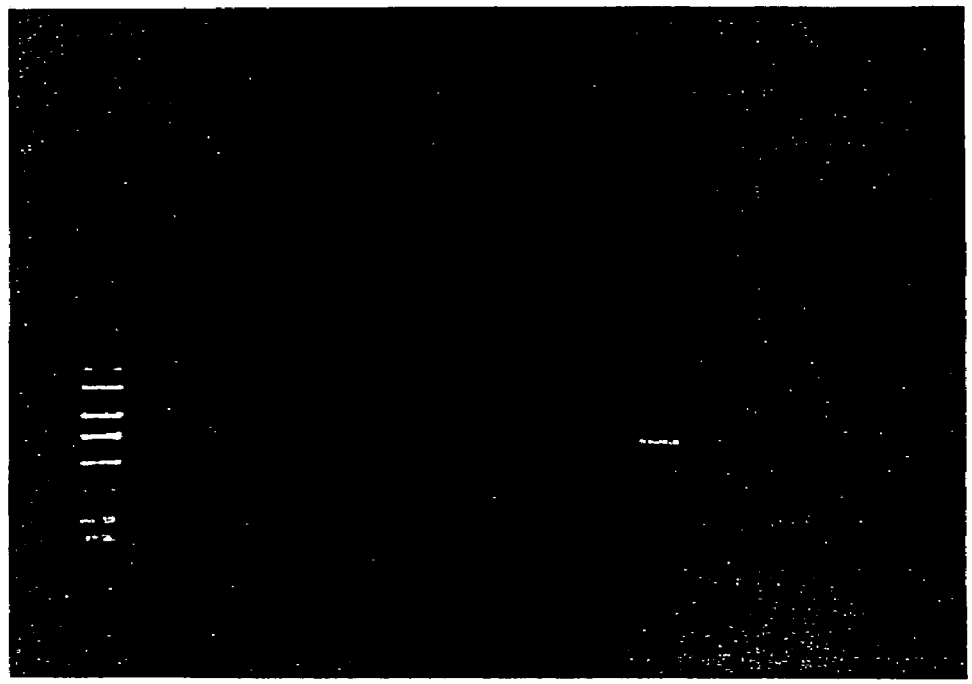

FIG. 14 shows the expression pattern of the ELF gene in 10 human tissue plus retinal pigment epithelium-derived cell line ARPE19, as determined by RT-PCR amplification with 17 cycles. The expression is detected in human retina only.

Figure 15:
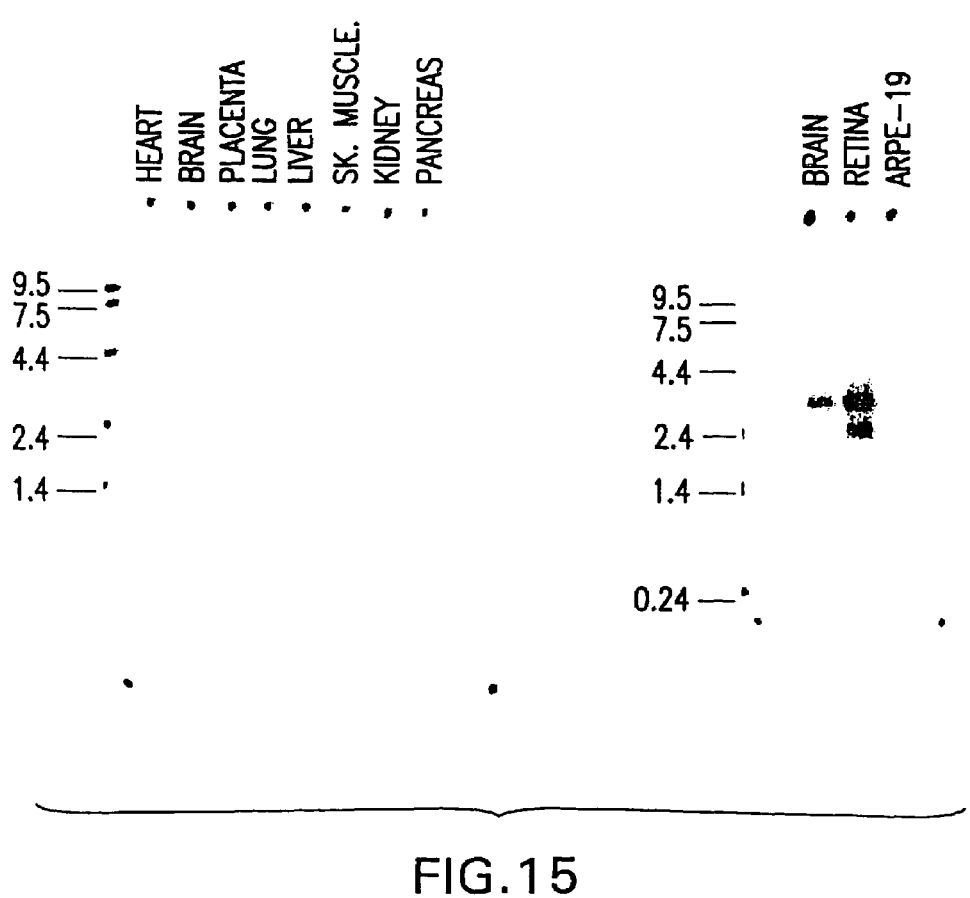

FIG. 15 shows the expression pattern of the human ELF gene in human tissues as determined by Northern blot hybridization. The expression is prominent in the human retina; the hybridization signal is also seen in the human brain. ELF mRNA exists in two different species, similar to what was reported for its only mammal relative, the Cig30 gene (Tvrdik et al 1999, *J. Biol. Chem.* 274:26387–26392).

FIG. 16 shows the 5'-regulatory region of human ELF gene. The initiating ATG codon in the first exon is shown in bold. Sequence elements that are common to mammalian RNA polymerase II promoters (CAAT box at position 1657 and four GC boxes at positions 1446, 1513, 1585, and 1744) are shown in bold and underlined.

As used through the specification and claims, the following definitions apply:

"Free from associated nucleic acids" means the nucleic acid is not covalently linked to a nucleic acid which is naturally linked to in an individual's chromosome.

"Free from associated proteins" means the ELF protein is not located in its native cell membrane; or in the case of the mutant allele, the mutant ELF is not located in the retinal cytoplasm where it normally is found.

This invention relates to the identification and characterization of the mutant allele responsible for Stargardt-like macular dystrophy. The designation of the gene is EFL (for Elongation of Fatty Acids).

Essential fatty acids (EFAs) are polyunsaturated fatty acids that cannot be manufactured by mammals, yet are required for a number of important biochemical processes, and thus must be supplied in the diet. The most important dietary EFAs are linoleic acid and alpha-linolenic acid (ALA). These two EFAs undergo a number of biosynthetic reactions that convert them into various other EFAs. FIG. 10 depicts the biosynthetic reactions involving the two groups of EFAs, the n-6 EFAs (linoleic acid derivatives) and the n-3 EFAs (ALA derivatives). EFAs are formed from linoleic acid and ALA by a series of alternating reactions involving the removal of two hydrogens coupled with the insertion of an additional double bond (desaturation) and the lengthening of the fatty acid chain by the addition of two carbons (chain elongation). The end product of the ALA pathway is docosahexaenoic acid (DHA).

Decosahexaenoic fatty acid (DHA) is a highly polyunsaturated, long-chain fatty acid, which has six double bonds and is 22 carbons in length [indicated as 22:6 (n-3), where the first number indicates chain length, the second number indicates the number of double bonds, and "n-3" indicates the position of the first double bond as its relates to the terminal methyl group]. DHA is a critical component of membranes in vertebrate retina, comprising up to 50% of all fatty acids in photoreceptor cells. While not wishing to be bound by theory, it appears the normal allele of ELF is involved in one of the elongation steps during DHA synthesis.

Bioinformatic analysis revealed a weak but significant homology between ELF and a group of two yeast proteins (Elo2p and Elo3p), whose function are also the elongation of fatty acids. The Kyte-Doolittle algorithm (FIG. 11) predicts that ELF has a transmembrane organization involving five transmembrane regions which is similar to the reported transmembrane organization of Elo2p and Elo3p. The Elo2p and Elo3p proteins are necessary for the synthesis of very long chain fatty acids of up to 24 and 26 carbon atoms, respectively (Oh et al. 1997, *J. Biol. Chem.* 272:17376–17384, which is hereby incorporated by reference). It seems that human ELF protein is responsible for the biosynthesis of DHA, as it requires the elongation up to 24 carbon atoms with subsequent chain shortening (beta-peroxidation) to 22 carbon atoms.

The mutant (i.e. disease-causing allele) of ELF contains a 5 bp deletion starting at bp 797. This results in a frameshift mutation from this position through the remainder of the C-terminus. The mutation removes the C-terminal region of the ELF protein which is reasonably conserved between human and mouse (see FIG. 8). Evolutionary conservation indicates functional significance of the protein region removed as a result of the frameshift mutation. In addition, the frameshift mutation removes the targeting signal in the C-terminus which is the same sequence as those known to be responsible for targeting proteins to the endoplasmic reticulum (Gaynor et al. 1994 *J. Cell Biol.* 127:653–665 and Schroder et al. 1995 *J. Cell Biol.* 131:895–912, both of which are incorporated by reference). This would prevent ELF protein from trafficking to the site of biosynthesis of very long chain fatty acids (membranes of the endoplasmic reticulum) Thus, deficiencies in the biosynthesis of DHA or other retina-specific fatty acids with very long chain resulting from mutations in ELF would predictably lead to retinal dysfunction.

There are additional observations which indicate that the genes of this invention are involved in Stargardt-like macular dystrophy. First of all, the mutant (disease-causing allelic form) has been identified in three independent families with Stargardt-like macular dystrophy. Secondly, the gene maps to the genetically defined region on human chromosome 6q14, which has been identified with Stargardt-like macular dystrophy. The ELF gene maps to the PAC clone dJ94c4 which is located in close vicinity of the genetic marker D6S460. The maximum reported lod score for D6S460 was 9.3, which is a clear indication of genetic proximity of this marker to the disease locus (Edwards et al. 1999, *Am. J. Ophthal.* 127:426–435.) Further, this gene was found to be exclusively expressed in the retina, specifically, in the photoreceptor cells (see FIGS. 13, 14, and 15).

Nucleic Acids

Thus, one aspect of this invention are nucleic acids which encode either the normal allele or the mutant allele of ELF; these nucleic acids may be free from associated nucleic acids. Preferably the source of the nucleic acids is a human; although this invention includes other mammalian forms, such as mouse, rat, pig, monkey and rabbit. Genes encoding ELF from a non-human mammal can be obtained by using the human DNA as a probe in libraries of the retina using standard biotechnological techniques, and one aspect of this invention is a method of isolating a non-human nucleic acid encoding an ELF protein comprising probing a retinal library of a non-human mammal. The probe is preferably from the human or mouse DNA, As used throughout the specification and claims, the term "gene" specifically refers to the protein-encoding portion of the gene, i.e. the structural gene, and specifically does not include regulatory elements such as promoters, enhancers, transcription termination regions and the like. The gene may be a cDNA or it may be an isolated form of genomic DNA. As used herein, "isolated" means that the DNA is physically separated from the DNA which it is normally covalently attached to in the chromosome. This includes DNA with a heterologous promoter and DNA which has its native regulatory sequences, but is not present in its native chromosome.

The ELF genes of this invention (both allelic forms) may have their own regulatory sequences operatively linked, or one may, using known biotechnology techniques, operatively linked heterologous regulatory regions. Such regulatory regions are well known, and include such promoters as the CMV promoter, rod-specific promoter of the rodopsin gene, retinal pigment epithelium-specific promoters of bestrophin or RPE65 genes. Commercially available mammalian expression vectors which are suitable for the expression of human ELF DNA include, but are not limited to: pMC1neo (Stratagene), pSG5 (Stratagene), pcDNAI and pcDNAIamp, pcDNA3, pcDNA3.1, pCR3.1 (Invitrogen), EBO-pSV2-neo (ATCC 37593), pBPV-1(8-2) (ATCC 37110), pdBPV-MMTneo (342-12) (ATCC 37224), pRS-Vgpt (ATCC 37199), pRSVneo (ATCC 37198), and pSV2-dhfr (ATCC 37146).

The ELF genes (regardless of species and allelic form) and operatively linked regulatory regions (an "ELF expression cassette) may be placed in a vector for transfer into a host cell. Vectors which are preferred include plasmids and, to a lesser degree, viral vectors. The choice of vector will often be dependent upon the host cell chosen. Cells which are preferred host cells include but are not limited to: ARPE-19, RPE-J, Y79, L cells L-M(TK⁻) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

A further aspect of this invention is a method of making an ELF protein (either a mutant or normal allelic form) comprising culturing a host cell comprising an ELF expression cassette, and recovering ELF protein. Alternatively a ELF gene may be integrated into a chromosome of the host cell, rather than being located on a vector. The resultant ELF-expressing cell lines (comprising a heterologous ELF gene, whether on a vector or in a host's chromosome) make up yet another aspect of this invention.

ELF Protein

Another aspect for this invention is an allelic form of ELF protein (normal or mutant) which is free from associated proteins. In a preferred embodiment the protein is mammalian, and in more preferred embodiments, the protein is a human form.

Still another aspect of this invention is a method for treating, preventing or lessening the severity of Stargardt-like macular degeneration comprising administering the normal allelic form of ELF to an individual at risk of the disease or who manifests the symptoms of the disease. The normal allelic form of ELF is preferably recombinantly produced. The normal ELF can substitute for the defective ELF made by these individuals, and perform the normal transporting function. The administration of the ELF protein is preferably in the form of a pharmaceutical composition comprising pharmaceutically acceptable diluents, excipients, and optionally stabilizers or preservatives. A typical pharmaceutical composition comprises 0.1 to 95% protein and is administered once, twice or three times daily. The pharmaceutical composition is preferably in the form of eyedrops, solutions or suspensions for subretinal and intravitreal injections, or slow release pellets.

Still another aspect of this invention is a method for in vitro bio-synthesis of fatty acids with a very long chain, for example DHA. Biosynthesis of DHA involves several elongation and desaturation steps (see FIG. 10).

We have previously identified and patented a retina-specific delta 6 desaturase called CYB5RP (U.S. Provisional Application Ser. No. 60/103,760; PCT/US99/23253, which is hereby incorporated by reference). CYB5RP is homologous to a delta 6 desaturase from *Borago oficinalis*. Both CYB5RP and this *Borago* delta 6 desaturase, unlike desaturases from higher plants, are unusual in containing a cytochrome b5-like domain fused to their N-termini (Sayanova et al., 1997, *Proc. Natl. Acad. Sci. USA* 94:4211–4216; hereinafter "Sayanova", which is hereby incorporated by reference). The *Borago* desaturase has been expressed in transgenic tobacco, resulting in high levels of delta 6 desaturated fatty acids in the transgenic tobacco leaves, including high levels of γ-linolenic acid (GLA) (Sayanova). Similarly, CYB5RP, expressed in transgenic plants (e.g., tobacco) is expected to provide a valuable source of GLA. Co-expression of the ELF cDNA in the same plant would predictably couple elongation and desaturation steps required for the production of DHA. Thus, CYB5RP and ELF DNA, co-expressed in transgenic plants, is expected to provide a valuable source of the important nutrient-docosahexaenoeic acid (DHA). The protocols for expression of foreign genes in plants are well developed and reported in the literature (Sayanova).

Animal Model

Another aspect of this invention is the use of mouse ELF DNA or mouse ELF protein corresponding to the normal or mutant form of human ELF for generating an animal model (knock-out or transgenic) that can be used for testing anti-AMD compounds. Oligonucleotide primers designed from the mouse cDNA sequence (SEQ.ID.NOS. 6) can be used to PCR amplify a fragment of the mouse ELF gene from the DNA of 129-strain embryonic stem cells (DNA of the 129Sv/J lambda genomic library is available from Stratagen). This genomic fragment can be used to generate a construct that will, upon electroporation into the 129-strain ES cells, generate a null mutation (targeted disruption) of the ELF gene. ES clones that have undergone homologous recombination with the construct can be injected into C57BL/6 blastocysts. Injected blastocytes can be transplanted into the uterus of pseudopregnant female mice. Their progeny can be selected for the germline transmission of the disrupted ELF gene and bred with 129SVEV females. The animals with heterozygous disruption of the mouse ELF gene can be bred to homozygosity.

The art of constructing the knock-out and transgenic mouse models is well-described in the literature and exemplified in Weng et al., 1999 *Cell* 98:13–23, which is hereby incorporated by reference.

Assays for Mutant Forms

Another aspect of this invention is an assay to identify individuals who are at risk for developing the symptoms of Stargardt-like macular dystrophy. The children of a person who has this disease are at risk, as the disease is inherited in a dominant-Mendelian fashion. Thus, if one parent does not have the disease, and the second parent is a heterozygous afflicted patient, the children have a 50% probability of developing the disease. As the children begin life with normal eyesight, there is time to intervene with protein therapy to reduce the severity, delay onset, or even completely prevent the symptoms from developing.

One assay in accordance with this invention is a labeled nucleic acid probe which spans the portion of the nucleic acid just 5' to the area where the mutant deletion occurs, and includes base pairs after the deletion, which include the frameshift mutation. Referring to the normal allele (SEQ.ID.NO. 3), a probe would be of any convenient length, preferably about 15 to 35 bp in length, more preferably at least about 25–30 base pairs in length. It would include a desired number of base pairs up to 796, skip 797–801, and resume at 802. The probe can be constructed so that it would hybridize to the sense strand, or alternatively so that hybridization occurs with the anti-sense strand. A typical probe would thus comprise (where the superscripted numeral correspond to base pair positions according to the normal allele): $C^{790}$ $T^{791}$ $T^{792}$ $T^{793}$ $C^{794}$ $T^{795}$ $T^{796}$ $C^{802}$ $T^{803}$ $A^{804}$ $C^{805}$ $A^{806}$ $T^{807}$ $T^{808}$ $C^{809}$ (SEQ.ID.NO. 14). The probe may contain additional 5' and or 3'-terminus base pairs which are essentially identical to those in the normal allele, so that the length of the probe is at least 15 bp long, and preferably at least 25 bp long. Generally the probe includes a detection means, such as a detectable label. Such labels, including radiolabels or fluorescent labels are well known in the art.

In an alternative embodiment, the probe would include base pairs which would hybridize to the normal allelic form of the ELF gene, but would not hybridize to the mutant form.

Another embodiment of this invention is a method of determining if an individual is at risk of developing Stargardt-like macular dystrophy comprising obtaining a sample of the ELF protein produced by the individual, and determining whether it is the normal or mutant form. This is preferably done by determining if an antibody specific for the normal allele of the ELF protein binds to the protein produced by the individual. In an alternate embodiment of this assay, the antibody is specific for the mutant form of ELF.

The antibodies of these assays may be polyclonal antibodies or monoclonal antibodies. The antibodies can be raised against the C-terminal peptide which is different in normal and mutant ELF proteins. The antibodies can be raised against the allele-specific synthetic C-terminal peptides that are coupled to suitable carriers, e.g., serum albumin or keyhole limpet hemocyanin, by methods well known in the art. Methods of identifying suitable anti genic fragments of a protein are known in the art. See, e.g., Hopp & Woods, 1981, *Proc. Natl. Acad. Sci.* 78:3824–3828; and Jameson & Wolf, 1988, CABIOS (Computer Applications in the Biosciences) 4:181–186, both of which are hereby incorporated by reference.

For the production of polyclonal antibodies, ELF protein or an antigenic fragment, coupled to a suitable carrier, is injected on a periodic basis into an appropriate non-human host animal such as, e.g., rabbits, sheep, goats, rats, mice. The animals are bled periodically and sera obtained are tested for the presence of antibodies to the injected antigen. The injections can be intramuscular, intraperitoneal, subcutaneous, and the like, and can be accompanied with adjuvant.

For the production of monoclonal antibodies, ELF protein or an antigenic fragment, coupled to a suitable carrier, is injected into an appropriate non-human host animal as above for the production of polyclonal antibodies. In the case of monoclonal antibodies, the animal is generally a mouse. The animal's spleen cells are then immortalized, often by fusion with a myeloma cell, as described in Kohler & Milstein, 1975, *Nature* 256:495–497. For a fuller description of the production of monoclonal antibodies, see *Antibodies: A Laboratory Manual*, Harlow & Lane, eds., Cold Spring Harbor Laboratory Press, 1988.

Normal and mutant ELF proteins differ in size (normal ELF is 41 amino acid longer which translates in the 4 kiloDalton difference on the SDS-PAGE). Such a difference can be easily detected, so antibodies against the common parts of the two proteins can be used on Western blots to detect the presence of the mutant ELF.

Gene Therapy

Gene therapy may be used to introduce ELF polypeptides into the cells of target organs, e.g., the photoreceptor cells, pigmented epithelium of the retina or other parts of the retina. Nucleotides encoding ELF polypeptides can be ligated into viral vectors which mediate transfer of the nucleotides by infection of recipient cells. Suitable viral vectors include retrovirus, adenovirus, adeno-associated virus, herpes virus, vaccinia virus, and polio virus based vectors. Alternatively, nucleotides encoding ELF polypeptides can be transferred into cells for gene therapy by non-viral techniques including receptor-mediated targeted transfer using ligand-nucleotide conjugates, lipofection, membrane fusion, or direct microinjection. These procedures and variations thereof are suitable for ex vivo as well as in vivo gene therapy. Gene therapy with ELF polypeptides will be particularly useful for the treatment of diseases where it is beneficial to elevate ELF activity.

Promoter/5-regulatory region of the ELF gene can be used in suitable viral and non-viral vectors to target the expression of other genes specifically in the photoreceptor cells of the human retina, due to the unique photoreceptor cell specificity of the ELF gene transcription. FIG. 16 shows the promoter for human ELF.

The following non-limiting Examples are presented to better illustrate the invention.

EXAMPLE 1

Identification of the ELF Gene and cDNA Cloning

Identification of the PAC (P1 Artificial Chromosome) Clone Containing the ELF Gene Genetics mapping clearly demonstrated the linkage of the autosomal dominant Stargardt-like macular dystrophy gene to the genetics markers on human chromosome 6q14 (Edwards et al., 1999 *Am. J. Ophthalmol.* 127: 426–435; Griesinger et al., 2000 *Inv. Ophthamol. Vis. Sci.* 41: 248–255; Stone et al.1994, *Arch. Ophthalmol.* 112: 765–772; each of which is incorporated by reference). The highest lod-score in the three papers cited above was reported by Edwards et al. for the genetic marker D6S460. The DNA sequence for D6S460 is available from the public DNA database (GenBank accession number Z24323).

DNA sequence from D6S460 was compared with GenBank database entries using the BLASTN algorithm. This comparison revealed that D6S460 is contained within the DNA sequence of PAC dJ75K24 (GenBank accession number AL035700).

The analysis of the physical map of human chromosome 6 available from the web site of The Sanger Centre (http://www.sanger.ac.uk/HGP/Chr6/) revealed that dJ75K24 overlaps with another PAC clone dJ159 G1 which in turn overlaps with PAC dJ92C4. These three PAC clones were chosen for the detailed bioinformatic analysis.

While complete DNA sequences were available for PACs 75k24 and 159G19 (GenBank accession numbers AL035700 and AL078462, respectively), the database entry for PACs 92c4 represented 11 unordered DNA pieces generated in Phase 1 High Throughput Genome Sequence Project (HTGS phase 1)—GenBank accession number AL132875. DNA sequences of PACs 75k24, 159G19, as well as the DNA sequences of 11 fragments from PAC 92c4 were compared with GenBank database entries using the BLASTN and BLASTX algorithms.

This comparison revealed the presence of two potential exons in PAC 92c4 whose DNA sequences, when translated, demonstrated significant homology with the members of the yeast ELO family known to be involved in elongation of fatty acids. Based on this homology, the novel human gene found in PAC 92s4 was designated ELF (Elongation of Fatty Acids); the two potential exons within PAC 92c4 were later defined as exons 2 and 4 of the human ELF gene (see FIG. 7)

cDNA sequencing, identification additional exons and exon/intron organization of the ELF gene.

The DNA sequence of the cDNA fragment that matches exons 2 and 4 was deduced from the genomic sequence of PAC 94c2. To identify additional exon(s) that may be located between exons 2 and 4, forward and reverse PCR primers from these exons of the ELF gene were synthesized and used to PCR amplify ELF cDNA fragments from human retina "Marathon-ready" cDNA (Clontech, Palo Alto, Calif.). In this RT-PCR experiment forward primer from ex2 (63exDL1: GTG TGG AAA ATT GGC CTC TG) (SEQ.ID.NO. 15) was paired with a reverse primer from ex4 (63exER1: GTC CTC CTG CAA CCC AGT TA) (SEQ.ID.NO. 16). A 50 µl PCR reaction was performed using the Taq Gold DNA polymerase (Perkin Elmer, Norwalk, Conn.) in the reaction buffer supplied by the manufacturer with the addition of dNTPs, primers, and approximately 0.5 ng of human retina cDNA. Cycling conditions were as follows: 1) 94° C., for 10 min; 2) 94° C. for 30 sec; 3) 72° C. for 2 min (decrease this temperature by 1.1° C. per cycle); 4) 72° C. for 2 min; 5) Go to step 2 fifteen more times; 6) 94° C. for 30 sec; 7) 55° C. for 2 min; 8) 72° C. for 2 min; 9) Go to step 6 twenty four more times; 10). 72° C. for 7 min; and 11) 4° C.

The PCR product was electrophoresed on a 2% agarose gel and DNA band was excised, purified and subjected to sequence analysis with the same primers that were used for PCR amplification. DNA sequence analysis was performed using the ABI PRISM™ dye terminator cycle sequencing ready reaction kit with AmpliTaq DNA polymerase, FS (Perkin Elmer, Norwalk, Conn.). Following linear amplification in a Perkin-Elmer 9600, the extension products were purified and analyzed on an ABI PRISM 377 automated sequencer (Perkin Elmer, Norwalk, Conn.).

The assembly of the DNA ,sequence results of this PCR product revealed that there is an additional exon between exons 2 and 4; it was later designated exon 3. This finding defined the order of the exons in ELF cDNA fragment as 5'-ex2-ex3-ex4-3'. Comparison of the DNA sequence of exon 3 with the DNA sequence of PAC 92c4 confirmed its location between exons 2 and 4 and revealed the description of intronic sequences flanking this exon.

The DNA sequence of exon 4 was compared with the EST database using the BlastN algorithm in an attempt to identify additional cDNA sequences. This analysis identified a mouse skin EST (GenBank accession number AA791133) with very high degree of similarity to exon 4 of the human ELF gene. The DNA sequence of the mouse skin EST AA791133 was compared with the genomic sequence of PAC 92c4. Despite the differences between the mouse and human sequences caused by evolutionary divergence, this analysis was able to reveal two additional human exons with PAC 94c4; there were later called exons 5 and 6. This finding defined the order of the exons in ELF cDNA as 5'-ex2-ex3-ex4-ex5-ex6-3'.

To verify the exonic composition of the cDNA that relied at the moment on identification of exons within the genomic sequence, forward and reverse PCR primers from known exons of the ELF gene were synthesized and used to PCR amplify CG1CE cDNA fragments from human retina "Marathon-ready" cDNA (Clontech, Palo Alto, Calif.). In these RT-PCR experiments forward primer from ex2 (63exDL1: GTG TGG AAA ATT GGC CTC TG) (SEQ.ID.NO. 15) was paired with a reverse primer from ex6 (63exHR1: CAT GGC TGT TTT TCC AGC TT) (SEQ.ID. NO. 17). Forward primer from ex5 (63exGL1: CCC AGT TGA ATT CCT TTA TCC A) (SEQ.ID.NO. 18) was paired with a reverse primer from ex6 (63exH_Right: GTC AAC AAC AGT TAA GGC CCA) (SEQ.ID.NO.19).

A 50 µl PCR reaction was performed using the Taq Gold DNA polymerase (Perkin Elmer, Norwalk, Conn.) in the reaction buffer supplied by the manufacturer with the addition of dNTPs, primers, and approximately 0.5 ng of human retina cDNA. PCR products were electrophoresed on a 2% agarose gel and DNA bands were excised, purified and subjected to sequence analysis with the same primers that were used for PCR amplification. The assembly of the DNA sequence results of these PCR products confirmed the cDNA sequence assembled from ELF exons and corrected the sequencing errors present in the database entry for PAC 92c4.

Identification of the 5' of the ELF cDNA

RACE is an established protocol for the analysis of cDNA ends. This procedure was performed using the Marathon RACE template from human retina, purchased from Clontech (Palo Alto, Calif.). cDNA primer from exon 2 (63exDR1: AGG TTA AGC AAA ACC ATC CCA) (SEQ.ID.NO. 20) in combination with a cDNA adaptor primer AP1 (CCA TCC TAA TAC GAC TCA CTA TAG GGC) (SEQ.ID.NO.:21) were used in 5' RACE.

After the initial PCR amplification, a nested PCR reaction was performed using nested adaptor primer AP2 (ACT CAC TAT AGG GCT CGA GCG GC) (SEQ.ID.NO.:22) and gene specific primer 63exDR2 (AGG TTC TCG GTC CTT CAT CC) (SEQ.ID.NO.:23). The PCR product was separated from the unincorporated dNTP's and primers using Qiagen, QIAquick PCR purification spin columns using standard protocols and resuspended in 30 µl of water. The products were analyzed on ABI 377 sequencers according to standard protocols. The PCR fragment obtained in the 5'RACE reaction was assembled into a contig with the ELF cDNA fragment covering exons 2 to 6; the DNA sequence of the resulted cDNA encodes a full-length ELF protein; the order of the exons in ELF cDNA was defined as 5'-ex1-ex2-ex3-ex4-ex5-ex6-3'

Comparison of the DNA sequences obtained from RT-PCR fragments with genomic sequence obtained from PAC 92c4 was performed using the program Crossmatch. This analysis determined Exact sequence of exon/intron boundaries within the ELF gene for all 6 exons. The splice signals in all introns conforms to published consensus sequences. Description of the flanking intronic sequences for each of the exons allowed the design of PCR primers for amplification of the ELF gene exons from the DNA of affected and nonaffected individuals from families with Stargardt-like dominant macular dystrophy.

EXAMPLE 2

Stargardt-Like Dominant Macular Dystrophy is Associated With the 5-bp Deletion in the Evolutionary Conserved Region of the ELF Gene Genomic DNA from the patients and control individuals from three pedigrees having dominant Stargardt-like macular dystrophy (families A, C, and D) was amplified by PCR using the following primer pair:

63exH_Left (GAA GAT GCC GAT GTT GTT AAA AG) (SEQ.ID.NO.:24)

63exH_Right (GTC AAC AAC AGT TAA GGC CCA) (SEQ.ID.NO. 19)

This primer pair amplifies a genomic fragment that contains exon 6 and an adjacent intronic region.

PCR products produced using the primer sets mentioned above were amplified in 50 µl reactions consisting of Perkin-Elmer 10×PCR Buffer, 200 mM dNTP's, 0.5 µl of Taq Gold (Perkin-Elmer Corp., Foster City, Calif.), 50 ng of patient DNA and 0.2 µM of forward and reverse primers. Cycling conditions were as follows: 1) 94° C. for 10 min; 2) 94° C.

for 30 sec; 3) 72° C. for 2 min (decrease this temperature by 1.1° C. per cycle); 4) 72° C. for 2 min; 5) Go to step 2 fifteen more times; 6) 94° C. for 30 sec. 7) 55° C. for 2 min; 8) 72° C. for 2 min; 9) Go to step 6 twenty four more times; 10) 72° C. for 7 min; and 11) 4° C.

Products obtained from this PCR amplification were analyzed on 2% agarose gels and excised fragments from the gels were purified using Qiagen QIAquick spin columns and sequenced using ABI dye-terminator sequencing kits. The products were analyzed on ABI 377 sequencers according to standard protocols.

The results of this experiment in four individuals from family A is shown in FIG. 12. The figure shows a small branch of this pedigree and four sequencing runs (boxed) of PCR fragments that represent exon 6 and adjacent intronic regions of the human ELF gene. From left to right, the runs are from A40 (father, unaffected with Stargardt-like dominant macular dystrophy), A4 (mother, affected with Stargardt-like dominant macular dystrophy), A430 (son of A4 and A40, unaffected with Stargardt-like dominant macular dystrophy), A43 (daughter of A4 and A40, affected with Stargardt-like dominant macular dystrophy). Reading the boxed chromatograms from left to right, the 5-base pair deletion shows up as appearance of double peaks starting from position 7 in the case of patients A4 and A43. This disease mutation was not found upon sequencing of 50 normal unrelated individuals (100 chromosomes) of North American descent.

EXAMPLE 3

Expression Studies of the ELF Gene

RT-PCR

RT-PCR experiments were performed on "quick-clone" human cDNA samples available from Clontech, Palo Alto, Calif. ARPE-19 cDNA was prepared according to standard protocols. cDNA samples from heart, brain, placenta, lung, liver, skeletal muscle, kidney, pancreas, retina, testis, and human retinal pigment epithelium cell line ARPE-19 were amplified with primers 63exGL1 (CCC AGT TGA ATT CCT TTA TCC A) (SEQ.ID.NO. 18) and 63exHR1 (CAT GGC TGT TTT TCC AGC TT) (SEQ.ID.NO. 17) in the following PCR conditions: 1) 94° C. for 10 min; 2) 94° C. for 30 sec; 3) 72° C. for 2 min (decrease this temperature by 1.1° C. per cycle); 4) 72° C. for 2 min; 5) Go to step 2 fifteen more times; 6) 94° C. for 30 sec; 7) 55° C. for 2 min; 8) 72° C. for 2 min; 9) Go to step 6 seventeen more times; 10) 72° C. for 7 min; and 11) 4° C.

The ELF gene was found to be expressed in human retina only (FIG. 14).

Northern Blot Analysis

Northern blots containing poly(A+)-RNA from different human tissues were purchased from Clontech, Palo Alto, Calif. The blot contained human heart, brain placenta, lung, liver, skeletal muscle, kidney, and pancreas poly(A+)-RNA.

A custom-made blot containing human retina, brain, and ARPE-19 poly(A+)-RNA was ordered from FRP Grating. Primers 63exDL1 (GTG TGG AAA ATT GGC CTC TG) (SEQ.ID.NO. 15) and 63exHR1 (CAT GGC TGT TTT TCC AGC TT) (SEQ.ID.NO.17) were used to amplify a PCR product from the "quick-clone" human retina cDNA available from Clontech, Palo Alto, Calif. This product was purified on an agarose gel, and used as a probe in Northern blot hybridization. The probe was labeled by random priming with the Amersham Rediprime kit (Arlington Heights, Ill.) in the presence of 50–100 µCi of 3000 Ci/mmole [alpha $^{32}$P]dCTP (Dupont/NEN, Boston, Mass.). Unincorporated nucleotides were removed with a ProbeQuant G-50 spin column (Pharmacia/Biotech, Piscataway, N.J.). The radiolabeled probe at a concentration of greater than $1\times10^6$ cpm/ml in rapid hybridization buffer (Clontech, Palo Alto, Calif.) was incubated overnight at 65° C. The blots were washed by two 15 min incubations in 2×SSC, 0.1% SDS (prepared from 20×SSC and 20% SDS stock solutions, Fisher, Pittsburgh, Pa.) at room temperature, followed by two 15 min incubations in 1×SSC, 0.1% SDS at room temperature, and two 30 min incubations in 0.1×SSC, 0.1% SDS at 60° C. Autoradiography of the blots was done to visualize the bands that specifically hybridized to the radiolabeled probe.

The probe hybridized to an mRNA transcript that is uniquely expressed in the human retina (see FIG. 15). Weaker hybridization signal is also seen in the human brain. ELF mRNA exists in two different species, similar to what was reported for its only mammal relative, the Cig30 gene (Tvrdik et al., J. Biol. Chem., 1999, 274:26387–26392; which is hereby incorporated by reference).

In Situ Hybridization

Primers 63exGL1 (CCC AGT TGA ATT CCT TTA TCC A) (SEQ.ID.NO. 18) and 63exHR1 (CAT GGC TGT TTT TCC AGC TT) (SEQ.ID.NO. 17) were used to amplify a PCR product from the "quick-clone" human retina cDNA available from Clontech, Palo Alto, Calif. This product was subcloned into the pCR-Script vector (Stratagene) giving the plasmid called phumGL1/HR2. This plasmid served as a hybridization probe and represented a fragment of the human normal ELF cDNA with coordinates 561–771. In situ hybridization was carried out on sections of rhesus monkey retina according to standard protocols. Specific -expression is seen in the inner segments of photoreceptor cells with the antisense probe (left panel). Probe signal is seen in blue color; retinal layers are visualized with propidium iodide counterstain (red). Right panel shows the hybridization with the sense control probe (sense probe is not complementary to the ELF mRNA). Retinal layers are marked as RPE, retinal pigment epithelium; OS, outer segments of photoreceptors; IS, inner segments of photoreceptors; ONL, outer nuclear layer, OPL, outer plexiform layer; INL, inner nuclear layer; IPL, inner plexiform layer; GCL, ganglion cell layer.

What is claimed is:

1. An isolated Elongation of Fatty Acids (ELF) protein, free from associated proteins, comprising the amino acid sequence set forth in FIG. 3 (SEQ ID NO: 1).

2. An ELF protein of claim 1 that is encoded by the cDNA sequence set forth in FIG. 3 (SEQ ID NO: 3).

3. A composition comprising the protein of claim 1 and a pharmaceutically acceptable carrier.

4. A composition according to claim 3 wherein the composition is an ophthalmic composition.

5. A vector comprising an ELF expression cassette, wherein said expression cassette comprises cDNA sequence of SEQ ID NO: 3 encoding an ELF protein.

6. The vector of claim 5 further comprising operatively linked regulatory regions.

7. An isolated host cell comprising a vector of claim 6.

8. A method of making an ELF protein comprising culturing a host cell of claim 7 and recovering said ELF protein.

* * * * *

UNITED STATES PATENT AND TRADEMARK OFFICE
CERTIFICATE OF CORRECTION

PATENT NO. : 7,179,620 B2  
APPLICATION NO. : 11/477042  
DATED : February 20, 2007  
INVENTOR(S) : Konstantin Petrukhin, Wen Li and Kang Zhang It is certified that error appears in the above-identified patent and that said Letters Patent is hereby corrected as shown below:

On the Title page, following the heading ASSIGNEE:

Delete "Merck & Co., Inc., Rahway, NJ (US)" and insert

-- Merck & Co., Inc., Rahway, NJ (US);  
Johns Hopkins University, Baltimore, MD (US) --

Signed and Sealed this

Thirtieth Day of December, 2008

JON W. DUDAS  
*Director of the United States Patent and Trademark Office*

SEQUENCE LISTING

<160> NUMBER OF SEQ ID NOS: 24

<210> SEQ ID NO 1
<211> LENGTH: 314

```
<212> TYPE: PRT
<213> ORGANISM: Human

<400> SEQUENCE: 1

Met Gly Leu Leu Asp Ser Glu Pro Gly Ser Val Leu Asn Val Val Ser
 1               5                  10                  15

Thr Ala Leu Asn Asp Thr Val Glu Phe Tyr Arg Trp Thr Trp Ser Ile
            20                  25                  30

Ala Asp Lys Arg Val Glu Asn Trp Pro Leu Met Gln Ser Pro Trp Pro
        35                  40                  45

Thr Leu Ser Ile Ser Thr Leu Tyr Leu Leu Phe Val Trp Leu Gly Pro
    50                  55                  60

Lys Trp Met Lys Asp Arg Glu Pro Phe Gln Met Arg Leu Val Leu Ile
65                  70                  75                  80

Ile Tyr Asn Phe Gly Met Val Leu Leu Asn Leu Phe Ile Phe Arg Glu
                85                  90                  95

Leu Phe Met Gly Ser Tyr Asn Ala Gly Tyr Ser Tyr Ile Cys Gln Ser
            100                 105                 110

Val Asp Tyr Ser Asn Asn Val His Glu Val Arg Ile Ala Ala Ala Leu
        115                 120                 125

Trp Trp Tyr Phe Val Ser Lys Gly Val Glu Tyr Leu Asp Thr Val Phe
    130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
                165                 170                 175

Ala Gly Gly Gln Ala Phe Phe Gly Ala Gln Leu Asn Ser Phe Ile His
            180                 185                 190

Val Ile Met Tyr Ser Tyr Tyr Gly Leu Thr Ala Phe Gly Pro Trp Ile
        195                 200                 205

Gln Lys Tyr Leu Trp Trp Lys Arg Tyr Leu Thr Met Leu Gln Leu Ile
    210                 215                 220

Gln Phe His Val Thr Ile Gly His Thr Ala Leu Ser Leu Tyr Thr Asp
225                 230                 235                 240

Cys Pro Phe Pro Lys Trp Met His Trp Ala Leu Ile Ala Tyr Ala Ile
                245                 250                 255

Ser Phe Ile Phe Leu Phe Leu Asn Phe Tyr Ile Arg Thr Tyr Lys Glu
            260                 265                 270

Pro Lys Lys Pro Lys Ala Gly Lys Thr Ala Met Asn Gly Ile Ser Ala
        275                 280                 285

Asn Gly Val Ser Lys Ser Glu Lys Gln Leu Met Ile Glu Asn Gly Lys
    290                 295                 300

Lys Gln Lys Asn Gly Lys Ala Lys Gly Asp
305                 310

<210> SEQ ID NO 2
<211> LENGTH: 271
<212> TYPE: PRT
<213> ORGANISM: Human

<400> SEQUENCE: 2

Met Gly Leu Leu Asp Ser Glu Pro Gly Ser Val Leu Asn Val Val Ser
 1               5                  10                  15

Thr Ala Leu Asn Asp Thr Val Glu Phe Tyr Arg Trp Thr Trp Ser Ile
            20                  25                  30
```

```
Ala Asp Lys Arg Val Glu Asn Trp Pro Leu Met Gln Ser Pro Trp Pro
         35                  40                  45

Thr Leu Ser Ile Ser Thr Leu Tyr Leu Leu Phe Val Trp Leu Gly Pro
     50                  55                  60

Lys Trp Met Lys Asp Arg Glu Pro Phe Gln Met Arg Leu Val Leu Ile
 65                  70                  75                  80

Ile Tyr Asn Phe Gly Met Val Leu Leu Asn Leu Phe Ile Phe Arg Glu
                 85                  90                  95

Leu Phe Met Gly Ser Tyr Asn Ala Gly Tyr Ser Tyr Ile Cys Gln Ser
                100                 105                 110

Val Asp Tyr Ser Asn Asn Val His Glu Val Arg Ile Ala Ala Ala Leu
             115                 120                 125

Trp Trp Tyr Phe Val Ser Lys Gly Val Glu Tyr Leu Asp Thr Val Phe
        130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
                165                 170                 175

Ala Gly Gly Gln Ala Phe Phe Gly Ala Gln Leu Asn Ser Phe Ile His
                180                 185                 190

Val Ile Met Tyr Ser Tyr Tyr Gly Leu Thr Ala Phe Gly Pro Trp Ile
            195                 200                 205

Gln Lys Tyr Leu Trp Trp Lys Arg Tyr Leu Thr Met Leu Gln Leu Ile
        210                 215                 220

Gln Phe His Val Thr Ile Gly His Thr Ala Leu Ser Leu Tyr Thr Asp
225                 230                 235                 240

Cys Pro Phe Pro Lys Trp Met His Trp Ala Leu Ile Ala Tyr Ala Ile
                245                 250                 255

Ser Phe Ile Phe Leu Phe Leu Leu His Ser Asp Ile Gln Arg Ala
                260                 265                 270

<210> SEQ ID NO 3
<211> LENGTH: 972
<212> TYPE: DNA
<213> ORGANISM: Human

<400> SEQUENCE: 3
cgccgcgatg gggctcctgg actcggagcc gggtagtgtc ctaaacgtag tgtccacggc      60
actcaacgac acggtagagt tctaccgctg gacctggtcc atcgcagata gcgtgtgga     120
aaattggcct ctgatgcagt ctccttggcc tacactaagt ataagcactc tttatctcct    180
gtttgtgtgg ctgggtccaa aatggatgaa ggaccgagaa ccttttcaga tgcgtctagt    240
gctcattatc tataattttg ggatggtttt gcttaacctc tttatcttca gagagttatt    300
catgggatca tataatgcgg gatatagcta tatttgccag agtgtggatt attctaataa    360
tgttcatgaa gtcaggatag ctgctgctct gtggtggtac tttgtatcta aaggagttga    420
gtatttggac acagtgtttt ttattctgag aaagaaaaac aaccaagttt ctttccttca    480
tgtgtatcat cactgtacga tgtttacctt gtggtggatt ggaattaagt gggttgcagg    540
aggacaagca ttttttggag cccagttgaa ttcctttatc catgtgatta tgtactcata    600
ctatggggta actgcatttg gcccatggat tcagaaatat ctttggtgga acgataccct    660
gactatgttg caactgattc aattccatgt gaccattggg cacacggcac tgtctcttta    720
cactgactgc ccctttccca aatggatgca ctgggctcta attgcctatg caatcagctt    780
```

-continued

```
catatttctc tttcttaact tctacattcg gacatacaaa gagcctaaga aaccaaaagc    840
tggaaaaaca gccatgaatg gtatttcagc aaatggtgtg agcaaatcag aaaaacaact    900
catgatagaa aatggaaaaa agcagaaaaa tggaaaagca aaggagatt aaattgaact     960 gggccttaac tg                                                        972
```

<210> SEQ ID NO 4
<211> LENGTH: 967
<212> TYPE: DNA
<213> ORGANISM: Human

<400> SEQUENCE: 4

```
cgccgcgatg gggctcctgg actcggagcc gggtagtgtc ctaaacgtag tgtccacggc    60
actcaacgac acgtagagt tctaccgctg gacctggtcc atcgcagata agcgtgtgga    120
aaattggcct ctgatgcagt ctccttggcc tacactaagt ataagcactc tttatctcct    180
gtttgtgtgg ctgggtccaa aatggatgaa ggaccgagaa ccttttcaga tgcgtctagt    240
gctcattatc tataattttg ggatggtttt gcttaacctc tttatcttca gagagttatt    300
catgggatca tataatgcgg gatatagcta tatttgccag agtgtggatt attctaataa    360
tgttcatgaa gtcaggatag ctgctgctct gtggtggtac tttgtatcta aaggagttga    420
gtatttggac acagtgtttt ttattctgag aaagaaaaac aaccaagttt ctttccttca    480
tgtgtatcat cactgtacga tgtttacctt gtggtggatt ggaattaagt gggttgcagg    540
aggacaagca ttttttggag cccagttgaa ttcctttatc catgtgatta tgtactcata    600
ctatggggta actgcatttg gcccatggat tcagaaatat ctttggtgga aacgataccgt   660 gactatgttg caactgattc aattccatgt gaccattggg cacacggcac tgtctcttta    720
cactgactgc cccttcccca atggatgca ctgggctcta attgcctatg caatcagctt    780
catatttctc tttcttctac attcggacat acaaagagcc taagaaacca aaagctggaa    840
aaacagccat gaatggtatt tcagcaaatg gtgtgagcaa atcagaaaaa caactcatga    900
tagaaaatgg aaaaagcag aaaaatggaa agcaaaagg agattaaatt gaactgggcc      960
ttaactg                                                             967
```

<210> SEQ ID NO 5
<211> LENGTH: 312
<212> TYPE: PRT
<213> ORGANISM: Mus Musculus

<400> SEQUENCE: 5

```
Met Gly Leu Leu Asp Ser Glu Pro Gly Ser Val Leu Asn Ala Met Ser
 1               5                  10                  15

Thr Ala Phe Asn Asp Thr Val Glu Phe Tyr Arg Trp Thr Trp Thr Ile
                20                  25                  30

Ala Asp Lys Arg Val Ala Asp Trp Pro Leu Met Gln Ser Pro Trp Pro
            35                  40                  45

Thr Ile Ser Ile Ser Thr Leu Tyr Leu Leu Phe Val Trp Leu Gly Pro
        50                  55                  60

Lys Trp Met Lys Asp Arg Glu Pro Phe Gln Met Arg Leu Val Leu Ile
65                  70                  75                  80

Ile Tyr Asn Phe Gly Met Val Leu Leu Asn Leu Phe Ile Phe Arg Glu
                85                  90                  95

Leu Phe Met Gly Ser Tyr Asn Ala Gly Tyr Ser Tyr Ile Cys Gln Ser
               100                 105                 110
```

Val Asp Tyr Ser Asn Asp Val Asn Glu Val Arg Ile Ala Ala Ala Leu
        115                 120                 125

Trp Trp Tyr Phe Val Ser Lys Gly Val Glu Tyr Leu Asp Thr Val Phe
130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
                165                 170                 175

Ala Gly Gly Gln Ala Phe Phe Gly Ala Gln Met Asn Ser Phe Ile His
            180                 185                 190

Val Ile Met Tyr Ser Tyr Tyr Gly Leu Thr Ala Phe Gly Pro Trp Ile
        195                 200                 205

Gln Lys Tyr Leu Trp Trp Lys Arg Tyr Leu Thr Met Leu Gln Leu Val
    210                 215                 220

Gln Phe His Val Thr Ile Gly His Thr Ala Leu Ser Leu Tyr Thr Asp
225                 230                 235                 240

Cys Pro Phe Pro Lys Trp Met His Trp Ala Leu Ile Ala Tyr Ala Ile
                245                 250                 255

Ser Phe Ile Phe Leu Phe Leu Asn Phe Tyr Thr Arg Thr Tyr Asn Glu
            260                 265                 270

Pro Lys Gln Ser Lys Thr Gly Lys Thr Ala Thr Asn Gly Ile Ser Ser
        275                 280                 285

Asn Gly Val Asn Lys Ser Glu Lys Ala Leu Glu Asn Gly Lys Pro Gln
    290                 295                 300

Lys Asn Gly Lys Pro Lys Gly Glu
305                 310

<210> SEQ ID NO 6
<211> LENGTH: 1292
<212> TYPE: DNA
<213> ORGANISM: Mus Musculus

<400> SEQUENCE: 6
cagtcgccca cggtccatcg gagcctctct tctcgcccgc ttgtcgtacc tctcctcgcc      60
aagatggggc tgctggactc agagcccggc agcgtcctga acgcgatgtc cacggcattc     120
aacgacaccg tggagttcta tcgctggacc tggaccattg cagataaacg tgtagcagac     180
tggccgctga tgcagtctcc atggccaacg ataagcataa gcacgctcta tctcctgttc     240
gtgtggctgg gtccaaagtg gatgaaagac cgcgagccgt tccaaatgcg cttagtactc     300
ataatctata attttggcat ggttttgctt aaccttttca tcttcagaga gctattcatg     360
ggatcataca acgcaggata cagctatatt tgccagtcag tggattattc taatgatgtt     420
aatgaagtca ggatagcggc ggccctgtgg tggtattttg tatcgaaagg cgttgagtat     480
ttggacacag tgttttttat cctgaggaag aaaaacaacc aagtctcctt ccttcacgtg     540
taccaccact gcaccatgtt cactctgtgg tggattggaa tcaagtgggt ggctggaggc     600
caagcgtttt cgggcccca gatgaactct tcatccacg tgatcatgta ctcctactat      660
gggctgactg cgttcggccc ctggatccag aaatatcttt ggtggaagcg ataccctgacc    720 atgctgcagc tggtccagtt ccacgtgacc atcggacaca cagcactgtc tctctacacc     780 gactgccct tccccaagtg gatgcactgg gctctgatcg cctacgccat cagcttcatc      840
ttcctcttcc tcaacttcta cactcggaca tacaatgagc cgaagcagtc aaaaaccgga     900
aagacggcca cgaatggtat ctcatcgaac ggcgtgaata atcagagaa agcgttagaa      960

-continued

| | |
|---|---|
| aacgggaaac cccagaaaaa cgggaagcca aaaggagagt aaattgaact gggccttaac | 1020 |
| cggtagacag tgaggaaact cctgtgtcat tttaaaaagt tcaggggcaa cagaagcaga | 1080 |
| gggtctgggc tggggagaaa ggcagatagg gtctttgccc ttcagactga gtaaaacttt | 1140 |
| tcaatatatg gtacccagat gttttattta tgaagttttt attttaaaag tttttttttt | 1200 |
| attaaccctt catgttgtcc aaaaccaaag caaccccccaa tgtggacctt gggagccttt | 1260 |
| tctctgttaa cattccgcct tgggcaatgg gg | 1292 |

<210> SEQ ID NO 7
<211> LENGTH: 2395
<212> TYPE: DNA
<213> ORGANISM: Human
<220> FEATURE:
<223> OTHER INFORMATION: Variable length; some residues may be missing

<400> SEQUENCE: 7

| | |
|---|---|
| gccgccaccg cctccggggt cagccctctc tctgggtctc cgctttctcc tgccgccagc | 60 |
| gcccgctcat cgccgcgatg gggctcctgg actcggagcc gggtagtgtc ctaaacgtag | 120 |
| tgtccacggc actcaacgac acggtagagt ctaccgctg gacctggtcc atcgcaggta | 180 |
| aagccgctga cttccccatc ctcgctcggt ccccgcggg gggtcaccgg ccctggtct | 240 |
| cgcagctccc gggcccggcc ccacaggccc cgcgccctg cggctttcgg atgctgcgga | 300 |
| agccacttgc aggagtcagt attgtttctt tggtttttat accatgtatt ttttgttggg | 360 |
| actcaaagga cagtgatccg tatttagtca aattaggaaa ttaagttgaa acatcttgat | 420 |
| tcctaaaaag tgtatttat aaaacattta ctgattaatg aattttatgg tattttgttc | 480 |
| tctctataga taagcgtgtg gaaaattggc ctctgatgca gtctccttgg cctacactaa | 540 |
| gtataagcac tctttatctc ctgtttgtgt ggctgggtcc aaaatggatg aaggaccgag | 600 |
| aaccttttca gatgcgtcta gtgctcatta tctataattt tgggatggtt ttgcttaacc | 660 |
| tctttatctt cagagaggta tgtttttaag atcactttaa taattttcca aggttattgg | 720 |
| aaatttaaaa atgagaatgt gtaaaaccat aatcggaatg catgaaattt ttaatgcatt | 780 |
| tgaaattttt aaagaaaata ttgtgtttaa ataatttga aaggctacat tttgtatata | 840 |
| attgtgtttt taatgctgtg tttactaaaa ctttactaca aatattatta ctctttttcc | 900 |
| agttattcat gggatcatat aatgcgggat atagctatat ttgccagagt gtggattatt | 960 |
| ctaataatgt tcatgaagtc agggtaagta cattaaaaat actcttaatc agtaaaagtg | 1020 |
| gtttgatttt tataggcccc agtctgtgaa atccatgcc ttgtacattt tgtgcaatat | 1080 |
| acaaatgttt attttggast tacttacaat gagtataaac ccatacaata gtgtcatttt | 1140 |
| ggtgtttata acacgctttc cctttttaca gatagctgct gctctgtggt ggtactttgt | 1200 |
| atctaaagga gttgagtatt tggacacagt gttttttatt ctgagaaaga aaaacaacca | 1260 |
| agtttcttc cttcatgtgt atcatcactg tacgatgttt accttgtggt ggattggaat | 1320 |
| taagtgggtt gcaggaggac aaggtgagca ttttcaggaa tatactgctt gcgtttaatt | 1380 |
| gcatatatgt gttcagtgga aagcaatgag aacctaggac tttgacttga tctaccattt | 1440 |
| aacttgcttt catggttaat catttccatg ttcatttctt tttttttttt tttttttttt | 1500 |
| ttttgagatg gagtctcgct ctgtcaccag gctggagtgc agtggcgcga tctcggctca | 1560 |
| ctgcaacctc cacctcccgg gttccagcga ttctcctgcc tcagcctcct gagtagctgg | 1620 |
| gactacaggc acacaccacc acgcctagct aattttttgt atttttagta gagacagggt | 1680 |
| ttcaccatgt tggccaggat ggtaaaagat ctcttgacct tgtgatccgc catctcagtg | 1740 |

```
gcttactgcc taataaaatt ttctgtatct tgtaattacc tgttgttttt ctaaagcatt    1800
ttttggagcc cagttgaatt cctttatcca tgtgattatg tactcatact atgggttaac    1860
tgcatttggc ccatggattc agaaatatct ttggtggaaa cgatacctga ctatgttgca    1920
actggtgagt taaatgcttc caaagtttct tctggtaaaa tactgaaatt gtttaaattt    1980 gattaattt aaagtgcaat gtcattttag acaattttca gatgccgatg ttgttaaaag    2040
ttgtttacta ttcagattaa atgttttgtg ctgtcatttc tgtttttcag attcaattcc    2100
atgtgaccat tgggcacacg gcactgtctc tttacactga ctgccccttc cccaaatgga    2160
tgcactgggc tctaattgcc tatgcaatca gcttcatatt tctctttctt aacttctaca    2220
ttcggacata caaagagcct aagaaaccaa aagctggaaa acagccatg aatggtatt    2280 cagcaaatgg tgtgagcaaa tcagaaaaac aactcatgat agaaatgga aaaaagcaga    2340 aaatggaaa agcaaaagga gattaaattg aactgggcct taactgttgt tgaca       2395
```

<210> SEQ ID NO 8
<211> LENGTH: 347
<212> TYPE: PRT
<213> ORGANISM: Saccharomyces

<400> SEQUENCE: 8

```
Met Asn Ser Leu Val Thr Gln Tyr Ala Ala Pro Leu Phe Glu Arg Tyr
 1               5                  10                  15

Pro Gln Leu His Asp Tyr Leu Pro Thr Leu Glu Arg Pro Phe Phe Asn
            20                  25                  30

Ile Ser Leu Trp Glu His Phe Asp Asp Val Val Thr Arg Val Thr Asn
        35                  40                  45

Gly Arg Phe Val Pro Ser Glu Phe Gln Phe Ile Ala Gly Glu Leu Pro
    50                  55                  60

Leu Ser Thr Leu Pro Pro Val Leu Tyr Ala Ile Thr Ala Tyr Tyr Val
65                  70                  75                  80

Ile Ile Phe Gly Gly Arg Phe Leu Leu Ser Lys Ser Lys Pro Phe Lys
                85                  90                  95

Leu Asn Gly Leu Phe Gln Leu His Asn Leu Val Leu Thr Ser Leu Ser
            100                 105                 110

Leu Thr Leu Leu Leu Leu Met Val Glu Gln Leu Val Pro Ile Ile Val
        115                 120                 125

Gln His Gly Leu Tyr Phe Ala Ile Cys Asn Ile Gly Ala Trp Thr Gln
    130                 135                 140

Pro Leu Val Thr Leu Tyr Tyr Met Asn Tyr Ile Val Lys Phe Ile Glu
145                 150                 155                 160

Phe Ile Asp Thr Phe Phe Leu Val Leu Lys His Lys Lys Leu Thr Phe
                165                 170                 175

Leu His Thr Tyr His His Gly Ala Thr Ala Leu Leu Cys Tyr Thr Gln
            180                 185                 190

Leu Met Gly Thr Thr Ser Ile Ser Trp Val Pro Ile Ser Leu Asn Leu
        195                 200                 205

Gly Val His Val Val Met Tyr Trp Tyr Tyr Phe Leu Ala Ala Arg Gly
    210                 215                 220

Ile Arg Val Trp Trp Lys Glu Trp Val Thr Arg Phe Gln Ile Ile Gln
225                 230                 235                 240

Phe Val Leu Asp Ile Gly Phe Ile Tyr Phe Ala Val Tyr Gln Lys Ala
                245                 250                 255
```

```
Val His Leu Tyr Phe Pro Ile Leu Pro His Cys Gly Asp Cys Val Gly
            260                 265                 270

Ser Thr Thr Ala Thr Phe Ala Gly Cys Ala Ile Ile Ser Ser Tyr Leu
            275                 280                 285

Val Leu Phe Ile Ser Phe Tyr Ile Asn Val Tyr Lys Arg Lys Gly Thr
            290                 295                 300

Lys Thr Ser Arg Val Val Lys Arg Ala His Gly Gly Val Ala Ala Lys
305                 310                 315                 320

Val Asn Glu Tyr Val Asn Val Asp Leu Lys Asn Val Pro Thr Pro Ser
                325                 330                 335

Pro Ser Pro Lys Pro Gln His Arg Arg Lys Arg
            340                 345

<210> SEQ ID NO 9
<211> LENGTH: 345
<212> TYPE: PRT
<213> ORGANISM: Saccharomyces

<400> SEQUENCE: 9

Met Asn Thr Thr Thr Ser Thr Val Ile Ala Ala Val Ala Asp Gln Phe
1               5                   10                  15

Gln Ser Leu Asn Ser Ser Ser Cys Phe Leu Lys Val His Val Pro
            20                  25                  30

Ser Ile Glu Asn Pro Phe Gly Ile Glu Leu Trp Pro Ile Phe Ser Lys
            35                  40                  45

Val Phe Glu Tyr Phe Ser Gly Tyr Pro Ala Glu Gln Phe Glu Phe Ile
50                  55                  60

His Asn Lys Thr Phe Leu Ala Asn Gly Tyr His Ala Val Ser Ile Ile
65                  70                  75                  80

Ile Val Tyr Tyr Ile Ile Ile Phe Gly Gly Gln Ala Ile Leu Arg Ala
                85                  90                  95

Leu Asn Ala Ser Pro Leu Lys Phe Lys Leu Leu Phe Glu Ile His Asn
            100                 105                 110

Leu Phe Leu Thr Ser Ile Ser Leu Val Leu Trp Leu Leu Met Leu Glu
            115                 120                 125

Gln Leu Val Pro Met Val Tyr His Asn Gly Leu Phe Trp Ser Ile Cys
130                 135                 140

Ser Lys Glu Ala Phe Ala Pro Lys Leu Val Thr Leu Tyr Tyr Leu Asn
145                 150                 155                 160

Tyr Leu Thr Lys Phe Val Glu Leu Ile Asp Thr Val Phe Leu Val Leu
                165                 170                 175

Arg Arg Lys Lys Leu Leu Phe Leu His Thr Tyr His His Gly Ala Thr
            180                 185                 190

Ala Leu Leu Cys Tyr Thr Gln Leu Ile Gly Arg Thr Ser Val Glu Trp
            195                 200                 205

Val Val Ile Leu Leu Asn Leu Gly Val His Val Ile Met Tyr Trp Tyr
            210                 215                 220

Tyr Phe Leu Ser Ser Cys Gly Ile Arg Val Trp Trp Lys Gln Trp Val
225                 230                 235                 240

Thr Arg Phe Gln Ile Ile Gln Phe Leu Ile Asp Leu Val Phe Val Tyr
                245                 250                 255

Phe Ala Thr Tyr Thr Phe Tyr Ala His Lys Tyr Leu Asp Gly Ile Leu
            260                 265                 270

Pro Asn Lys Gly Thr Cys Tyr Gly Thr Gln Ala Ala Ala Ala Tyr Gly
            275                 280                 285
```

```
Tyr Leu Ile Leu Thr Ser Tyr Leu Leu Leu Phe Ile Ser Phe Tyr Ile
    290                 295                 300

Gln Ser Tyr Lys Lys Gly Lys Lys Thr Val Lys Lys Glu Ser Glu
305                 310                 315                 320

Val Ser Gly Ser Val Ala Ser Gly Ser Ser Thr Gly Val Lys Thr Ser
                325                 330                 335

Asn Thr Lys Val Ser Ser Arg Lys Ala
            340                 345

<210> SEQ ID NO 10
<211> LENGTH: 16
<212> TYPE: DNA
<213> ORGANISM: Human

<400> SEQUENCE: 10
tttcttaact tctaga                                               16

<210> SEQ ID NO 11
<211> LENGTH: 16
<212> TYPE: DNA
<213> ORGANISM: Human
<220> FEATURE:
<221> NAME/KEY: misc_feature
<222> LOCATION: (1)...(16)
<223> OTHER INFORMATION: n = A,T,C or G

<400> SEQUENCE: 11
tttcttannc attncn                                               16

<210> SEQ ID NO 12
<211> LENGTH: 16
<212> TYPE: DNA
<213> ORGANISM: Human

<400> SEQUENCE: 12
tttcttaact tctaca                                               16

<210> SEQ ID NO 13
<211> LENGTH: 16
<212> TYPE: DNA
<213> ORGANISM: Human
<220> FEATURE:
<221> NAME/KEY: misc_feature
<222> LOCATION: (1)...(16)
<223> OTHER INFORMATION: n = A,T,C or G

<400> SEQUENCE: 13
tttcttanac attcgg                                               16

<210> SEQ ID NO 14
<211> LENGTH: 15
<212> TYPE: DNA
<213> ORGANISM: Artificial Sequence
<220> FEATURE:
<223> OTHER INFORMATION: Probe

<400> SEQUENCE: 14
ctttcttcta cattc                                                15

<210> SEQ ID NO 15
<211> LENGTH: 20
<212> TYPE: DNA
<213> ORGANISM: Artificial Sequence
<220> FEATURE:
```

```
<223> OTHER INFORMATION: PCR Probe

<400> SEQUENCE: 15
gtgtggaaaa ttggcctctg                                                    20

<210> SEQ ID NO 16
<211> LENGTH: 20
<212> TYPE: DNA
<213> ORGANISM: Artificial Sequence
<220> FEATURE:
<223> OTHER INFORMATION: PCR Probe

<400> SEQUENCE: 16
gtcctcctgc aacccagtta                                                    20

<210> SEQ ID NO 17
<211> LENGTH: 20
<212> TYPE: DNA
<213> ORGANISM: Artificial Sequence
<220> FEATURE:
<223> OTHER INFORMATION: PCR Probe

<400> SEQUENCE: 17
catggctgtt tttccagctt                                                    20

<210> SEQ ID NO 18
<211> LENGTH: 22
<212> TYPE: DNA
<213> ORGANISM: Artificial Sequence
<220> FEATURE:
<223> OTHER INFORMATION: PCR Probe

<400> SEQUENCE: 18
cccagttgaa ttcctttatc ca                                                 22

<210> SEQ ID NO 19
<211> LENGTH: 21
<212> TYPE: DNA
<213> ORGANISM: Artificial Sequence
<220> FEATURE:
<223> OTHER INFORMATION: PCR Probe

<400> SEQUENCE: 19
gtcaacaaca gttaaggccc a                                                  21

<210> SEQ ID NO 20
<211> LENGTH: 21
<212> TYPE: DNA
<213> ORGANISM: Artificial Sequence
<220> FEATURE:
<223> OTHER INFORMATION: PCR Probe

<400> SEQUENCE: 20
aggttaagca aaaccatccc a                                                  21

<210> SEQ ID NO 21
<211> LENGTH: 27
<212> TYPE: DNA
<213> ORGANISM: Artificial Sequence
<220> FEATURE:
<223> OTHER INFORMATION: PCR Probe

<400> SEQUENCE: 21
ccatcctaat acgactcact atagggc                                            27
```

```
<210> SEQ ID NO 22
<211> LENGTH: 23
<212> TYPE: DNA
<213> ORGANISM: Artificial Sequence
<220> FEATURE:
<223> OTHER INFORMATION: PCR Probe

<400> SEQUENCE: 22
actcactata gggctcgagc ggc                                              23

<210> SEQ ID NO 23
<211> LENGTH: 20
<212> TYPE: DNA
<213> ORGANISM: Artificial Sequence
<220> FEATURE:
<223> OTHER INFORMATION: PCR Probe

<400> SEQUENCE: 23
aggttctcgg tccttcatcc                                                  20

<210> SEQ ID NO 24
<211> LENGTH: 23
<212> TYPE: DNA
<213> ORGANISM: Artificial Sequence
<220> FEATURE:
<223> OTHER INFORMATION: PCR Probe

<400> SEQUENCE: 24
gaagatgccg atgttgttaa aag                                              23
```